United States Patent
Fontes et al.

(10) Patent No.: US 10,433,538 B2
(45) Date of Patent: Oct. 8, 2019

(54) COMPOSITIONS AND METHODS FOR ORGAN PRESERVATION

(71) Applicants: Paulo Artur Chaves Fontes, Pittsburgh, PA (US); William R. Light, Cambridge, MA (US)

(72) Inventors: Paulo Artur Chaves Fontes, Pittsburgh, PA (US); William R. Light, Cambridge, MA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 487 days.

(21) Appl. No.: 14/435,082

(22) PCT Filed: Oct. 11, 2013

(86) PCT No.: PCT/US2013/064607
§ 371 (c)(1),
(2) Date: Apr. 10, 2015

(87) PCT Pub. No.: WO2014/059316
PCT Pub. Date: Apr. 17, 2014

(65) Prior Publication Data
US 2015/0230453 A1    Aug. 20, 2015

Related U.S. Application Data

(60) Provisional application No. 61/713,284, filed on Oct. 12, 2012.

(51) Int. Cl.
*A01N 1/02* (2006.01)
(52) U.S. Cl.
CPC ......... *A01N 1/0226* (2013.01); *A01N 1/0247* (2013.01)
(58) Field of Classification Search
None
See application file for complete search history.

(56) References Cited

U.S. PATENT DOCUMENTS

| | | | |
|---|---|---|---|
| 4,879,283 A * | 11/1989 | Belzer | A01N 1/02 435/1.2 |
| 5,405,742 A | 4/1995 | Taylor | |
| 5,723,282 A * | 3/1998 | Fahy | A01N 1/02 435/1.2 |
| 5,753,616 A | 5/1998 | Rausch et al. | |
| 5,895,810 A | 4/1999 | Light et al. | |
| 5,955,581 A | 9/1999 | Rausch et al. | |
| 6,794,124 B2 | 9/2004 | Steen | |
| 6,953,655 B1 | 10/2005 | Hassanein et al. | |
| 6,994,954 B2 | 2/2006 | Taylor | |
| 7,255,983 B2 * | 8/2007 | Steen | A01N 1/02 435/1.1 |
| 7,459,535 B2 | 12/2008 | Page et al. | |
| 7,678,563 B2 | 3/2010 | Wright et al. | |
| 7,811,808 B2 | 10/2010 | Van Der Plaats et al. | |
| 7,993,681 B2 * | 8/2011 | Roth | A01N 1/02 424/708 |
| 8,268,612 B2 | 9/2012 | Owen et al. | |
| 2002/0128182 A1 | 9/2002 | Gawryl et al. | |
| 2004/0038192 A1 * | 2/2004 | Brasile | A01N 1/0226 435/1.2 |
| 2004/0241634 A1 | 12/2004 | Millis et al. | |
| 2006/0063142 A1 | 3/2006 | Owen et al. | |
| 2010/0028850 A1 | 2/2010 | Brassil | |
| 2010/0151435 A1 | 6/2010 | Thatte et al. | |
| 2010/0209532 A1 * | 8/2010 | Dube | A61K 9/0026 424/606 |
| 2010/0234928 A1 | 9/2010 | Rakhorst et al. | |
| 2011/0200981 A1 | 8/2011 | Doubleday | |

FOREIGN PATENT DOCUMENTS

| | | | |
|---|---|---|---|
| CN | 101433712 B * | 10/2011 | ............. A61K 38/06 |
| WO | WO 2009/041806 | 4/2009 | |

OTHER PUBLICATIONS

Luer et al., Role of oxygen during hypothermic machine perfusion preservation of the liver, Transplant International, 23 (2010) 944-950.*

Vekemans et al., Artificial Circulation of the Liver: Machine Perfusion as a Preservation Method in Liver Transplantation, The Anatomical Record 291:735-740 (2008).*

Plaats et al., Hypothermic Machine Preservation in Liver Transplantation Revisited: Concepts and Criteria in the New Millennium, Annals of Biomedical Engineering, vol. 32, No. 4, Apr. 2004 (© 2004) pp. 623-631.*

Vairetti et al., Subnormothermic Machine Perfusion Protects Against Rat Liver Preservation Injury: A Comparative Evaluation With Conventional Cold Storage, Transplantation Proceedings, 39, 1765-1767 (2007).*

Muhlbacher et al., Preservation Solutions for Transplantation, Transplantation Proceedings, 31, 2069-2070 (1999).*

Badylak et al., "Engineered whole organs and complex tissues," Lancet, vol. 379, pp. 943-952, 2012.

Cole et al., "Effect of Oncotic Pressure of Diaspirin Cross-Linked Hemoglobin (DCLHb™) on Brain Injury After Temporary Focal Cerebral Ischemia in Rats," Anesthesia & Analgesia, vol. 83, pp. 342-347, 1996.

(Continued)

Primary Examiner — Louise W Humphrey
Assistant Examiner — Srikanth Patury
(74) Attorney, Agent, or Firm — Klarquist Sparkman, LLP

(57) ABSTRACT

Disclosed herein are solutions for use with machine perfusion of one or more organs. In some embodiments, the solutions comprise acellular cross-linked hemoglobin in a physiologically acceptable medium. Also disclosed herein are methods for machine perfusion of one or more organs, for example utilizing the disclosed perfusion solutions. In some embodiments, the methods include perfusing an organ with an oxygenated solution (such as the disclosed solutions) which is at a temperature between about 12-37° C., for example at a temperature of about 21° C.

12 Claims, 15 Drawing Sheets

(56) References Cited

OTHER PUBLICATIONS

Contaldo et al., "New generation of hemoglobin-based oxygen carrier evaluated for oxygenation of critically ischemic hamster flap tissue," *Crit., Care Med.*, vol. 33, No. 4, pp. 806-812, 2005.

Fondevila et al., "Hypothermic Oxygenated Machine Perfusion in Porcine Donation After Circulatory Determination of Death Liver Transplant," *Transplantation*, vol. 94, No. 1, pp. 22-29, 2012.

Gage et al., "Room Temperature Pulsatile Perfusion of Renal Allografts With Lifor Compared With Hypothermic Machine Pump Solution," *Transplantation Proceedings*, vol. 41, pp. 3571-3574, 2009.

Harris et al., "Modern Cross-Linking Strategies for Synthesizing Acellular Hemoglobin-Based Oxygen Carriers," *Biotechnol. Prog.*, vol. 24, pp. 1215-1225, 2008.

Jahr et al., "HBOC-201, hemoglobin glutamer-250 (bovine), Hemopure® (Biopure Corporation)," *Expert Opin. Biol. Ther.*, vol. 8, No. 9, pp. 1425-1433, 2008.

Levy et al., "Polymerized bovine hemoglobin solution as a replacement for allogeneic red blood cell transfusion after cardiac surgery: Results of a randomized, double-blind trial," *Journal of Thoracic and Cardiovascular Surgery*, vol. 124, pp. 35-42, 2002.

Levy, "The use of haemoglobin glutamer-250 (HBOC-201) as an oxygen bridge in patients with acute anaemia associated with surgical blood loss," *Expert Opin., Biol., Ther.*, vol. 3, No. 3, pp. 509-517, 2003.

Lifeblood Medical, Inc., "Lifor® as a Blood Surrogate for Donated Organs," www.lifebloodmedical.com, 2012 (9 pages).

Organ Assist, "When time counts and quality saves lives," http://www.organ-assist.nl/home.html, retrieved on Sep. 25, 2012 (5 pages).

Organ Recovery Systems, "SPS-1® Static Preservation Solution (UW Solution)," http://www.organ-recovery.com/pdfs/SPS1/SPS-1_Brochure.pdf, 2012 (2 pages).

St. Peter et al., "Liver and kidney preservation by perfusion," *Lancet*, vol. 359, pp. 604-613, 2002.

XVIVO Perfusion, "The Gold Standard in Lung Preservation," http://www.xvivoperfusion.com/products/cold-preservation/perfadex/, retrieved on Oct. 3, 2012 (2 pages).

Yeter et al., "Organ preservation with the organ care system," *Applied Cardiopulmonary Pathophysiology*, vol. 15, pp. 207-212, 2011.

\* cited by examiner

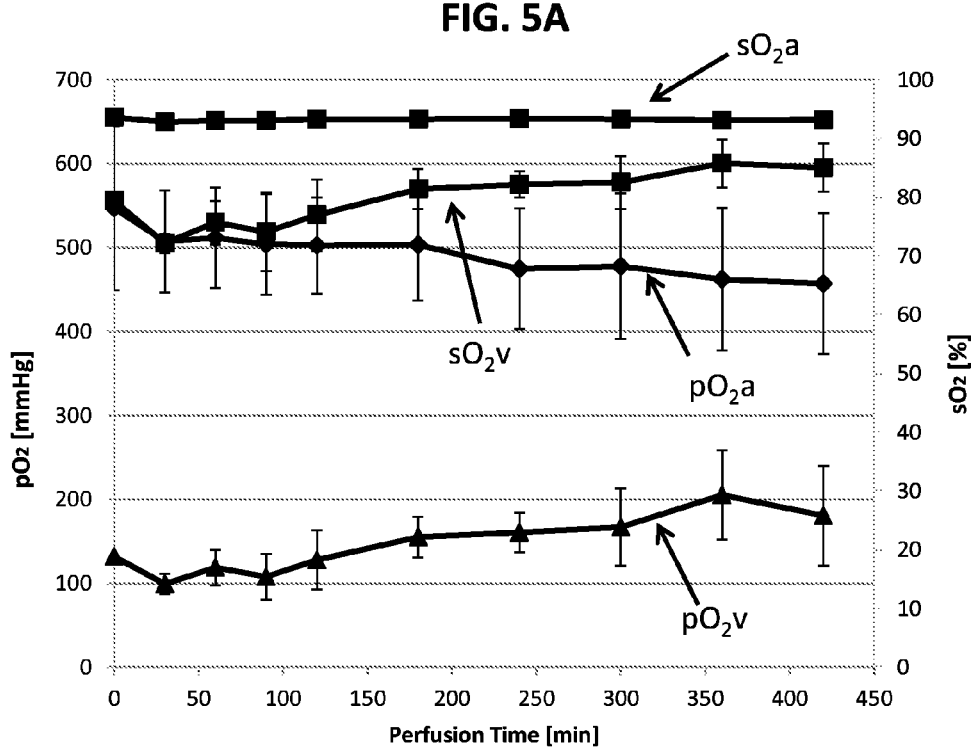
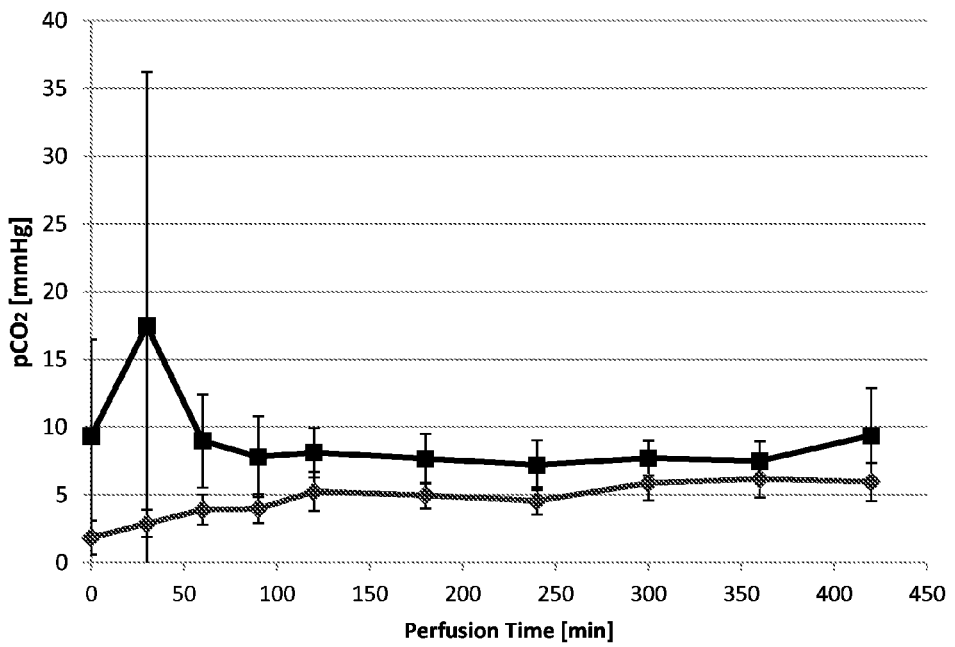

FIG. 13C  FIG. 13D
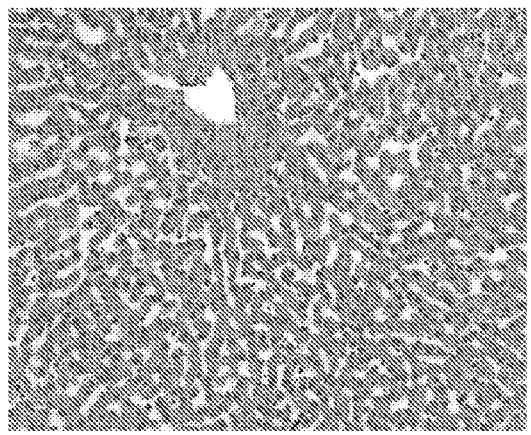
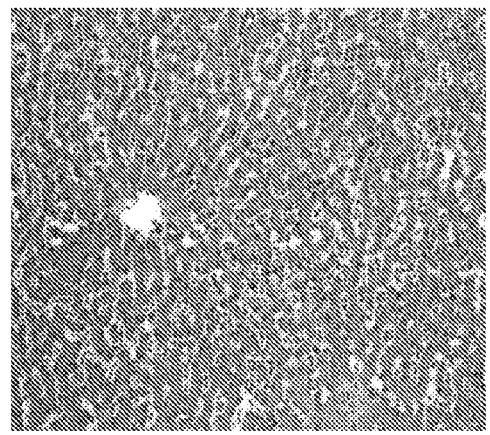
FIG. 13E
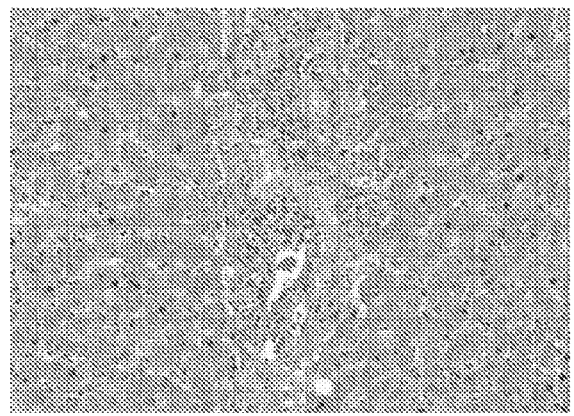

COMPOSITIONS AND METHODS FOR ORGAN PRESERVATION

CROSS REFERENCE TO RELATED APPLICATIONS

This is the § 371 U.S. National Stage of International Application No. PCT/US2013/064607, filed Oct. 11, 2013, which was published in English under PCT Article 21(2), which in turn claims the benefit of U.S. Provisional Application No. 61/713,284, filed Oct. 12, 2012, which is incorporated herein by reference in its entirety.

FIELD

This disclosure relates to solutions and methods for preserving or enhancing organs, particularly during machine perfusion.

BACKGROUND

Machine perfusion was conceived of as a way to ameliorate organ preservation long before the full development of clinical transplantation in the 1960s. The University of Wisconsin (UW) solution became the gold standard for cold static preservation in clinical transplantation in the 1980s, while machine perfusion remained a secondary option for organ preservation.

The exponential expansion of clinical transplantation created a greater demand for cadaveric organs since the life-saving organs (e.g., liver, heart, lungs) could not be recovered from live donors. Transplant candidates' waiting times have continued to grow around the world, imposing further morbidity and mortality for this population. Transplant centers have continued to be pushed towards the utilization of expanded criteria organs while the market faces a new supply/demand crisis limited by the current standards in organ preservation. The effective expansion of organ transplantation remains severely limited by cold static preservation with UW solution (or other solutions, such as HTK, CELSIOR, IGL-1, POLYSOL, or VASOSOL solutions), which has not decreased the number of discarded organs. The quality of the organs decreases during the limited amount of time given by cold static preservation (e.g. 4 hours for a heart allograft), since the tissues are unable to function or achieve any degree of regeneration while being kept under severe hypothermia (4° C.) and under anoxic conditions. Meanwhile, the discard rates of human organs have continued to increase in spite the high mortality rate on the transplant waiting lists (18 patients/day) in the United States.

Thus, there is a need to develop improved devices, methods, and preservation solutions in order to improve the success rate of organ transplantation and to decrease discard rates of organs.

SUMMARY

The ability to provide effective oxygenation to the organs and tissues while under machine perfusion presents several challenges. For example, mitochondrial enzymes are not able to function below about 12° C., making use of oxygen ineffective at the currently used temperature of 4° C. (even in the presence of oxygen carriers). Furthermore, the use of oxygen at low temperatures (below 12° C.) causes progressive generation of damaging reactive oxygen species by the mitochondria. Preservation solutions are not effectively able to carry oxygen if they do not include true oxygen carrier molecules (such as hemoglobin or perfluorocarbon). Machine perfusion devices should be able to provide adequate levels of oxygenation and flow, while perfusing the organ or tissue for longer periods of time. Finally, pulsatile pressures are biologically necessary to sustain adequate tissue perfusion in the arterial bed while encountering high resistance to the perfusate flow. Disclosed herein are solutions and methods for machine perfusion of one or more organs or tissues, such as composite tissue allografts (CTAs) (including, but not limited to ex vivo perfusion) that support mitochondrial function, reduce tissue damage, and maintain or even enhance organ function during perfusion.

Disclosed herein are solutions for use with machine perfusion of one or more organs. In some embodiments, the solutions comprise acellular cross-linked hemoglobin in a physiologically acceptable medium. In some examples, the solution has a pH of about 7.0-8.0 (for example, about 7.2-7.9) at room temperature, an osmolality of about 290-360 mOsm/kg, and a colloid osmotic pressure (COP) of about 18-75 mm Hg. In particular examples, the physiologically acceptable medium includes about 100-140 mM sodium ions, about 8-18 mM potassium ions, about 30-90 mM chloride ions, and about 0.2-0.7 mM calcium ions. In some examples, the solutions also include one or more osmotic agents that increase the osmolality of the solution.

Also disclosed herein are methods for machine perfusion of one or more organs, for example utilizing the disclosed perfusion solutions. In some embodiments, the methods include perfusing an organ with an oxygenated solution (such as the disclosed solutions) which is at a temperature between about 12-37° C. In particular embodiments, the solution is at a temperature of about 12-25° C., for example at a temperature of about 21° C.

The foregoing and other features of the disclosure will become more apparent from the following detailed description, which proceeds with reference to the accompanying figures.

BRIEF DESCRIPTION OF THE DRAWINGS

FIG. 1A shows portal vein (PV; left) and hepatic artery (HA; right) perfusion characteristics as follows: 1, flow (ml/min); 2, temperature (° C.); 3, pressure (mm Hg).

FIGS. 2A and 2B are from the same animal, taken after organ reperfusion and at necropsy a few hours after graft implantation, respectively. FIGS. 2C and 2D are from another animal, taken after organ reperfusion and at end-study necropsy ($5^{th}$ post-operative day), respectively.

(FIG. 3A) and lactate measurements during the perfusion (FIG. 3B).

FIG. 5A is a graph showing arterial blood gas (ABG) values obtained during the course of perfusion ($FiO_2$=60%).

FIG. 5B is a graph showing $pCO_2$ levels within the perfusate. Squares, $pCO_2v$; diamonds, $pCO_2a$.

FIGS. 13A-E are a series of digital images of liver biopsy histology in study group samples taken at 3 hours (FIG. 13A), 6 hours (FIG. 13B), and 9 hours (FIG. 13C) of perfusion, post-reperfusion (FIG. 13D), and at end-study necropsy (FIG. 13E).

FIG. 15A shows state 3 respiration. FIG. 15B shows state 4 respiration. FIG. 15C shows the respiratory control ratio.

DETAILED DESCRIPTION

Figure 1A:
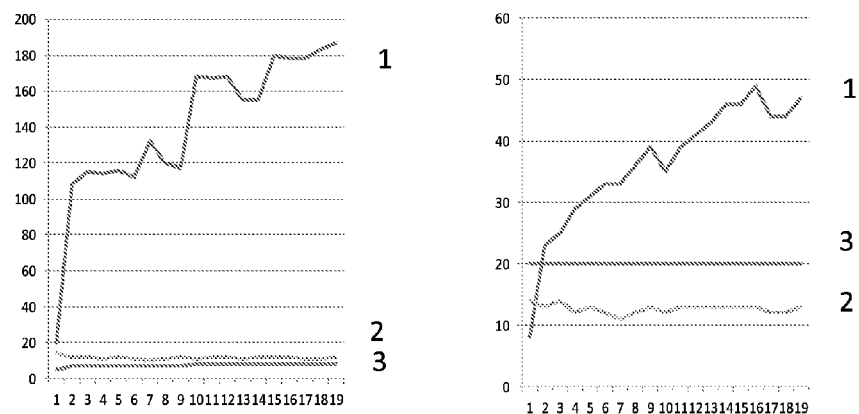
FIGS. 1A and B are pair of graphs showing perfusion characteristics using Belzer machine perfusion solution (BMP) in the liver perfusion device over nine hours at 12° C.

I. Abbreviations
ABG arterial blood gas
ALT alanine transaminase
AST aspartate transaminase
BMPS Belzer machine perfusion solution
CIT cold ischemia time
COP colloid osmotic pressure
CTA composite tissue allograft (or composite tissue allotransplantation)
$FiO_2$ fraction of inspired oxygen
HA hepatic artery
HBOC hemoglobin-based oxygen carrier
I/R ischemia-reperfusion
MAP mean arterial pressure
MPLD machine perfusion liver device
$pO_2$ partial pressure of oxygen
PV portal vein
RCR respiratory control ratio
VRAM vertical rectus myocutaneous flap II. Terms Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Colloid osmotic pressure (COP): Also referred to as oncotic pressure. The osmotic pressure generated in capillaries by colloids. Colloids refers collectively to large molecular weight (for example, >30,000 Da molecular weight) particles present in a solution. In normal plasma, the plasma proteins are the major colloids present, with albumin generating about 70-80% of the COP. The oncotic pressure of plasma is generally about 25-30 mm Hg.

Composite Tissue Allograft (CTA): A construct that includes multiple types of tissue, such as skin, muscle, tendon, cartilage, fat, bone, nerve, blood vessels, and/or other tissue types that is transplanted from (or may be transplanted from) one individual (a donor) to another individual (a recipient). In some examples, a composite tissue allograft is a limb or extremity (such as an arm, leg, hand, foot, finger, or toe), face (or portion thereof, such as lips, nose, and/or eyelids), larynx, or other body parts. In another example, a CTA includes a model construct, such as a myo-adipo-cutaneous flap (for example, a swine vertical rectus myocutaneous (VRAM) flap).

Hemoglobin-based oxygen carrier (HBOC): Molecules or compositions with oxygen carrying capabilities derived from the presence of hemoglobin. In some examples, HBOCs include isolated or purified hemoglobin (sometimes referred to as "acellular" HBOCs). Exemplary acellular HBOCs contain polymerized hemoglobin (for example, bovine or human hemoglobin), for example HBOC-201 (HEMOPURE, OPK Biotech, Cambridge, Mass.), HEMOLINK (Hemosol, Inc., Toronto, Canada), and POLY-HEME (Northfield Laboratories, Evanston, Ill.) or encapsulated hemoglobin (such as liposome- or polymersome-encapsulated hemoglobin). In other examples, HBOCs include red blood cells.

Organ: A part of the body, tissue, or portion thereof that can be transplanted or preserved ex vivo. Organs include, but are not limited to liver, kidney, heart, lung, pancreas, small intestine, and limb (such as arm or leg, or portion thereof), or extremity (such as hand, foot, finger, toe, or a portion thereof). As used herein, "organ" also includes other tissues, such as tissue grafts (also referred to as composite tissue allografts herein).

Osmolality: The number of osmoles of solute per kilogram of solvent. Osmolality is independent of pressure and temperature of the solution.

Osmotic agent: A substance to which capillary walls are impermeable. Osmotic agents contribute to the oncotic pressure exerted by a solution. Non-limiting examples of osmotic agents include albumin, hydroxyethyl starch, dextrose, mannitol, and ribose.

Perfusion: Circulation of a fluid (also referred to as a perfusion solution or perfusate) through an organ or CTA to supply the needs of the organ or CTA to retain its viability (for example, in an ex vivo system). In some examples, the perfusion solution includes an oxygen carrier (for example, a hemoglobin-based oxygen carrier). Machine perfusion refers to introduction and removal of a perfusion solution to an organ by a mechanical device. Such devices may include one or more chambers for holding an organ and a perfusion solution, one or more pumps for delivery of the perfusion solution to the organ, one or more means to regulate temperature of the perfusion solution, and one or more means to oxygenate the perfusion solution. In some examples, machine perfusion includes introduction of an oxygen carrying fluid into an organ and removal of oxygen depleted fluid from the organ by circulation of the oxygen carrying fluid through the organ.

In some embodiments, the perfusion can be pulsatile, with periodic increases and decreases of flow, to mimic arterial blood flow from a beating heart. In other embodiments, the perfusion can be continuous, with a substantial absence of flow rate variations, to mimic venous blood flow under most physiologic conditions.

III. Organ Perfusion Solutions

Disclosed herein are solutions for perfusion (for example, machine perfusion) of an organ. The solutions can be used for ex vivo perfusion of an organ, for example, for organ preservation during manipulation, treatment, storage and/or transport of an organ for transplantation in a recipient or reimplantation in a subject. In some embodiments, the solutions have characteristics such as oxygen-carrying capacity, pH, osmolality, and/or COP that make them particularly suitable for machine perfusion of an organ at sub-normothermic temperatures (such as about 12-25° C.), as discussed below. In some embodiments, the disclosed solutions include an oxygen carrier (such as acellular cross-linked hemoglobin) in a physiologically acceptable medium. In particular examples, the characteristics of the solution are provided as those when the solution is under storage conditions (for example, in a container at room temperature). The solution may have a pH of about 7.0-8.0 (such as about 7.2-7.9, for example, about 7.4-7.85) at room temperature, an osmolality of about 290-360 mOsm/kg, and a COP of about 18-75 mm Hg. Some exemplary, non-limiting perfusion solutions are provided herein, for example in Tables 1, 2, and 5.

In some embodiments, the disclosed organ perfusion solutions include acellular hemoglobin (for example, hemoglobin which is not contained in a cell, such as a red blood cell), which provides oxygen carrying capacity to the solution. In some embodiments, the acellular hemoglobin is cross-linked hemoglobin, such as cross-linked human or bovine hemoglobin. The protein component of hemoglobin is a heterotetramer of two α subunits and two β subunits. In some examples, cross-linking hemoglobin stabilizes the α-β dimers, making it more stable and also reducing its affinity for oxygen. In some examples, cross-linked hemoglobin also includes polymers of stabilized hemoglobin tetramers. The disclosed solutions include cross-linked hemoglobin, for example, cross-linked bovine hemoglobin having an average molecular weight of about 200-270 kD (such as about 250 kD). In some examples, the cross-lined bovine hemoglobin is glutaraldehyde cross-linked hemoglobin. Methods of cross-linking hemoglobin are described in, for example, U.S. Pat. Nos. 7,459,535; 7,135,554; 6,610,832; 6,552,173; 6,083,909; 5,770,727; and International Pat. Publ. No. WO 01/34648. One of ordinary skill in the art can identify additional methods of preparing cross-linked hemoglobin. An example of a solution including cross-linked hemoglobin is HEMOPURE solution (OPK Biotech, Cambridge, Mass.).

In other examples, the acellular hemoglobin includes encapsulated hemoglobin (such as liposome encapsulated hemoglobin or polymersome encapsulated hemoglobin). See, e.g., U.S. Pat. Nos. 5,674,528; and 5,688,526. In further embodiments, the oxygen carrier is not a hemoglobin-based oxygen carrier (for example, a synthetic oxygen carrier, such as a lipid heme microsphere). It is contemplated that the disclosed solutions and methods can utilize any acellular hemoglobin or other acellular oxygen carrier now known or developed in the future, provided that the hemoglobin (or oxygen carrier) can provide sufficient oxygen carrying capacity (for example, providing sufficient oxygenation and removal of carbon dioxide in a perfused organ, as discussed in the examples below).

The disclosed solutions utilize a low fraction of oxygen carrier (such as hemoglobin, for example acellular hemoglobin), for example compared to that found in blood. However, this amount surprisingly has been found to provide adequate oxygen delivery and carbon dioxide removal for organ preservation at sub-normothermic temperatures, while maintaining low levels of methemoglobin production. In addition, a low fraction of hemoglobin (such as cross-linked hemoglobin) reduces potential adverse effects of the presence of exogenous hemoglobin in the perfusate, including vasoactivity, nephrotoxicity, interference with macrophage function, antigenicity, indirect complement activation, and neurotoxicity. In some embodiments, the disclosed solutions contain about 3-10 g/dL of acellular hemoglobin (such as cross-liked bovine hemoglobin, for example glutaraldehyde cross-linked bovine hemoglobin), such as about 3-9 g/dL, about 3-8 g/dL, about 3-7 g/dL, about 3-6 g/dL, about 3-5 g/dL, or about 3-4 g/dL. In some examples, the solution contains about 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, or 10 g/dL cross-linked hemoglobin. In particular embodiments, the solutions include about 3-4 g/dL cross-linked bovine hemoglobin. In one non-limiting example, the solution includes about 3.25 g/dL cross-linked bovine hemoglobin.

As discussed above, the disclosed perfusion solutions have a pH of about 7.0-8.0 (such as about 7.2-7.9 or about 7.4-7.85) at room temperature, an osmolality of about 290-360 mOsm/kg (such as about 290-300 mOsm/kg), and a COP of about 18-75 mm Hg (such as about 35-65 mm Hg). In some embodiments, the solution has a pH (at room temperature) of about 7.0 to about 8.0, about 7.1 to about 7.9, about 7.2 to about 7.9, about 7.3 to about 7.8, about 7.4 to about 7.85, about 7.5 to about 7.75, about 7.6 to about 7.75, or about 7.6 to about 7.7. In particular non-limiting examples, the pH at room temperature is about 7.60, 7.61, 7.62, 7.63, 7.64, 7.65, 7.66, 7.67, 7.68, 7.69, or 7.70. In further embodiments, the osmolality of the solution is about 290-360 mOsm/kg, such as about 290-350, 290-330, 295-340, 300-310, 300-325, 310-350, 290-300, 290-299, 290-298, 290-297, 290-296, 295-300, 295-299, 295-298, 295-297, 295-296, 296-300, 296-299, or 298-300 mOsm/kg. In some examples, the osmolality of the solution is about 290, 290.5, 291, 291.5, 292, 292.5, 293, 293.5, 294, 294.5, 295, 295.5, 296, 296.5, 297, 297.5, 298, 298.5, 299, 299.5, or 300 mOsm/kg. In additional embodiments, the solution has a COP of about 18 to 75 mm Hg, for example about 20-70, 25-65, 30-70, 35-65, 35-60, 40-60, 40-50, 50-60, or 55-60 mm Hg. In some non-limiting examples, the COP of the solution is about 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 mm Hg. In some embodiments, the solution has a pH, osmolality, and COP selected from any one of the values provided herein. In one non-limiting example, the solution has a pH of about 7.6-7.7, an osmolality of about 295-297 mOsm/kg, and a COP of about 58-60 mm Hg, such as a pH of about 7.62, osmolality of about 296 mOsm/kg, and a COP of about 59 mm Hg.

The disclosed solutions include cross-linked hemoglobin in a physiologically acceptable medium. In some examples, a physiologically acceptable medium includes a solution that is isotonic (or nearly isotonic) with blood, such as Ringer's solution or a modified Ringer's solution (for example, lactated Ringer's solution). In some embodiments, the disclosed solutions include about 100-140 mM sodium ions, about 8-18 mM potassium ions, about 30-90 mM chloride ions, and about 0.2-0.7 mM calcium ions. In some examples, the solutions include about 100-110 mM sodium ions (such as about 100, 101, 102, 103, 104, 105, 106, 107, 108, 109, or 110 mM sodium ions), about 15-18 mM potassium ions (such as about 15, 16, 17, or 18 mM potassium ions), about 30-40 mM chloride ions (such as about 30, 31, 32, 33, 34, 35, 36, 37, 38, 39, or 40 mM chloride ions), and about 0.2-0.3 mM calcium ions (such as about 0.20, 0.21, 0.22, 0.23, 0.24, 0.25, 0.26, 0.27, 0.28, 0.29, or 0.30 mM calcium ions). In one non-limiting example, the solution includes about 105 mM sodium ions, about 17.3 mM potassium ions, about 36 mM chloride ions, and about 0.24 mM calcium ions.

The disclosed solutions may also contain one or more osmotic agents that increase the osmolality of the solution. Osmotic agents include substances to which capillary walls are impermeable. Exemplary osmotic agents include albumin, dextran, dextrose, mannitol, ribose, hydroxyethyl starch, polyethylene glycol (such as PEG-35), raffinose, and lactobionate. One or more osmotic agents can be used to adjust to the COP of a solution to the desired oncotic pressure. One of ordinary skill in the art can select additional osmotic agents that can be used in the disclosed solutions, so long as the final COP of the solution is about 18-75 mm Hg, such as about 35-65 mm Hg.

The disclosed solutions can include additional components, such as one or more reducing agents or buffers. In some examples, the solution includes a reducing agent, such as glutathione, N-acetyl-L-cysteine, or a combination thereof. One of ordinary skill in the art can select additional reducing agents that can be used in the solutions. In some examples, the disclosed solutions include about 0.5-3 mM glutathione (such as about 0.5, 1, 1.5, 2, 2.5, or 3 mM glutathione). In one example, the solution includes about 2.25 mM glutathione. In other examples, the disclosed solutions include about 40-160 mg/dL N-acetyl-L-cysteine (such as about 45-155, 50-150, 50-100, or 50-75 mg/dL N-acetyl-L-cysteine).

In other examples, the solution includes a buffer, such as HEPES ((4-(2-hydroxyethyl)-1-piperazineethanesulfonic acid). Additional buffers include, but are not limited to phosphate (such as sodium phosphate or potassium phosphate), citrate (such as sodium citrate), acetate (such as sodium acetate), or bicarbonate (such as sodium bicarbonate). One of ordinary skill in the art can select additional buffers that can be used in the disclosed solutions. In particular embodiments, the disclosed solutions include HEPES (such as about 2-8 mM HEPES, for example about 2, 2.5, 3, 3.5, 4, 4.5, 5, 5.5, 6, 6.5, 7, 7.5, or 8 mM HEPES) and/or 6-20 mM $KH_2PO_4$ (such as about 6-20 mM $KH_2PO_4$, for example, about 6-19, 7-18, 10-20, 15-20, 18-20, or 18-19 mM $KH_2PO_4$).

The solution may also contain one or more precursors of adenosine triphosphate, such as adenine. In some examples, the solution includes about 1-4 mM adenine, such as about 1, 1.5, 2, 2.5, 3, 3.5, or 4 mM adenine. Additional components, such as antibiotics (for example, penicillin), insulin, and/or dexamethasone can be added prior to using the solution, if desired.

Exemplary perfusion solutions are shown in Table 1. In particular examples, the perfusion solution includes 3-4 g/dL cross-linked hemoglobin, 25-30 mM NaCl, 1-2 mM KCl, 17-19 mM $KH_2PO_4$, 55-65 mM sodium gluconate, 6-8 mM sodium lactate, 3-4 mM magnesium gluconate, 0.6-0.8 mM $CaCl_2$ dihydrate, 15-16 mM NaOH, 3-4 mM adenine, 6-8 mM dextrose, 2-3 mM glutathione, 6-8 mM HEPES, 3-4 mM ribose, 20-25 mM mannitol, 35-40 g/L hydroxyethyl starch, and 40-60 mg/dL N-acetylcysteine. A particular non-limiting example of an organ perfusion solution of the disclosure is provided in Table 2.

TABLE 1

Exemplary organ perfusion solution components

| Component | Concentration |
|---|---|
| Cross-linked hemoglobin | 3-10 g/dL |
| NaCl | 25-85 mM |
| KCl | 1-3 mM |
| $KH_2PO_4$ | 6-20 mM |
| Sodium gluconate | 20-70 mM |
| Sodium lactate | 5-21 mM |
| Magnesium gluconate | 1-4 mM |
| $CaCl_2$-dihydrate | 0.6-1.2 mM |
| NaOH | 11-16 mM |
| Adenine | 1-4 mM |
| Dextrose | 2-8 mM |
| Glutathione | 0.5-3 mM |
| HEPES | 2-8 mM |
| Ribose | 1-4 mM |
| Mannitol | 7-30 mM |
| Hydroxyethyl starch | 10-40 g/L |
| N-acetyl-L-cysteine | 40-160 mg/dL |

TABLE 2

Exemplary organ perfusion solution

| Component | Concentration |
|---|---|
| Cross-linked hemoglobin | 3.25 g/dL |
| NaCl | 28.25 mM |
| KCl | 1 mM |
| $KH_2PO_4$ | 18.75 mM |
| Sodium gluconate | 60 mM |
| Sodium lactate | 6.75 mM |
| Magnesium gluconate | 3.75 mM |
| $CaCl_2$-dihydrate | 0.725 mM |
| NaOH | 15.62 mM |
| Adenine | 3.75 mM |
| Dextrose | 7.5 mM |

TABLE 2-continued

Exemplary organ perfusion solution

| Component | Concentration |
|---|---|
| Glutathione | 2.25 mM |
| HEPES | 7.5 mM |
| Ribose | 3.75 mM |
| Mannitol | 22.5 mM |
| Hydroxyethyl starch | 37.5 g/L |
| N-acetyl-L-cysteine | 50 mg/dL |

IV. Methods of Organ Perfusion

Disclosed herein are methods of organ perfusion (such as ex vivo organ perfusion or in situ organ perfusion). In some embodiments, the methods are used for ex vivo preservation of organ or composite tissue allografts, for example in which an organ or tissue is removed from a donor and preserved during storage and/or transport prior to implantation in a recipient. In other embodiments, the methods can also be used for autotransplantation, for example, in which an organ or tissue is temporarily removed for ex vivo therapy (such as resection of a tumor or gene therapy), followed by reimplantation. In further embodiments, the methods can be used to preserve or enhance ex vivo organ function, for example, prior to or during isolation of cells from an organ for further use (such as transplantation of cells into a donor). The disclosed methods can be used with any organ or tissue which can be machine perfused, including, but not limited to liver, kidney, heart, lung, pancreas, small intestine, or any portion thereof. In some examples, the disclosed methods can be used for more than one organ in combination, for example heart and lung(s). As used herein, the term "organ" also includes tissues, such as tissue allografts or composite tissue allografts (such as a finger, hand, arm, toe, foot, leg, face, or portion thereof).

In some embodiments, the methods include machine perfusion of one or more organs with an oxygenated perfusion solution disclosed herein (such as one of the perfusion solutions in Tables 1, 2, and 5). In some embodiments the temperature of the solution perfused into the organ is between about 12-37° C. (such as about 12-30° C., 20-32° C., 20-25° C., 12-28° C., 12-25° C., 12-21° C., 15-25° C., 15-22° C., 15-21° C., 15-20° C., or 20-22° C.). In some embodiments, a sub-normothermic temperature (such as about 20-32° C.) is selected for the perfusion solution. Sub-normothermic temperatures may provide particular advantages over hypothermic or normothermic temperatures. For example, mitochondrial function is maintained at temperatures above about 12° C., allowing maintenance of cellular ATP stores. In addition, decreasing temperatures below about 37° C. reduces the risk of infection by slowing or inhibiting bacterial growth. In some examples, the temperature of the solution perfused into the organ is about 12, 13, 14, 15, 16, 17, 18, 19, 20, 21, 22, 23, 24, 25, 26, 27, 28, 29, 30, 31, 32, 33, 34, 35, 36, or 37° C. In one non-limiting example, the temperature of the perfusion solution is about 21° C. when it is perfused into the organ. In additional embodiments, the temperature of the organ and/or the chamber holding the perfused organ is also maintained at the same temperature as the perfusate, for example by means of one or more thermo units connected to the organ chamber.

In some examples, the organ is not perfused with a solution less than about 12° C., for example, the organ is not perfused with a solution having a temperature of about 11, 10, 9, 8, 7, 6, 5, 4° C. or less. The organ may be flushed with cold (for example 4-10° C.) solutions, such as lactated Ringer's solution, UW solution, or other solutions prior to machine perfusion or prior to transplantation into a recipient in some examples. In other examples, the organ is not stored in a solution without perfusion (before and/or after machine perfusion) for more than about 1 hour.

In some examples, the organ is perfused with one of the disclosed solutions with oxygenation for a period of time to allow for storage and/or transport of the organ (for example from a donor site to a recipient site) prior to allogeneic transplantation; for surgical or clinical treatment of the organ (for example, resection of diseased or damaged tissue or introduction of pharmaceutical or gene therapy compositions), for example prior to retransplantation or allogeneic transplantation; or for removal of cells (such as isolation of cells for transplantation into a recipient) and/or introduction of new cells. In some embodiments, the organ is perfused for about 1 hour to about 14 days, such as about 1-72 hours, 2-48 hours, 4-24 hours, 1-14 days, 1-10 days, 1-7 days, 2-14 days, 2-10 days, or 5-10 days. In particular examples, the organ is perfused for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more hours or about 1, 2, 3, 4, 5, 6, 7, 8, 9, 10, 11, 12, 13, 14 or more days.

The disclosed methods include perfusing one or more organs with an oxygenated perfusion solution, such as a perfusion solution disclosed herein that has been oxygenated. Methods of oxygenating a perfusion solution are known to one of ordinary skill in the art. Machine perfusion devices (such as those described below) can include oxygenators for providing oxygenation of perfusion solutions. In some embodiments of the disclosed methods, the perfusion solution is oxygenated with a gas mixture including about 40-80% fraction inspired oxygen ($FiO_2$). In some examples, the perfusion solution is oxygenated with a gas mixture with $FiO_2$ of about 40-70%, about 40-65%, about 40-60%, or about 50-60%, such as about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80%. In particular examples, the $FiO_2$ of the oxygenation mixture is about 60%. The $FiO_2$ of the gas mixture used for oxygenation in some examples, may be an amount that could cause damage to the tissue (for example, greater than 40%); however without being bound by theory, it is believed that the reduced amount of hemoglobin in the perfusion solution prevents such damage. In other examples, the perfusion solution is oxygenated such that the $pO_2$ of the solution is about 300-720 mm Hg, such as about 325-710, 335-650, 350-600, 375-575, 400-550, or about 510-600 mm Hg.

The perfusion solution is delivered to the organ via one or more cannulas which are inserted in a vessel of the organ (such as an artery or vein), for example a vessel that supplies blood (such as oxygenated blood) to an organ. One of ordinary skill in the art can select appropriate vessels for perfusion of an organ. For example, a kidney may be perfused through a cannula inserted in the renal artery, while a liver may be perfused through a cannula inserted in the hepatic artery and/or a cannula inserted in the portal vein, a heart may be perfused through one or more cannulas inserted in the coronary arteries, and lungs may be perfused through one or more cannulas inserted in the pulmonary arteries. In other examples, a CTA may be perfused through a cannula inserted in an artery of the CTA. In some embodiments, the flow of the perfusion solution to the organ is a continuous flow, such as a flow without substantial variations of flow rate, for example to mimic venous blood flow under most physiologic conditions. In other embodiments, the flow of the perfusion solution to the organ is a pulsatile flow (such as having flow rate variations that mimic arterial pulsatile blood flow), for example, pulsatile flow of the perfusion solution through a cannula inserted in an artery of the organ or CTA. In some examples, the pulsatile flow of the perfusion solution is with a pulse of about 50-70 beats per minute (such as about 50, 51, 52, 53, 54, 55, 56, 57, 58, 59, 60, 61, 62, 63, 64, 65, 66, 67, 68, 69, or 70 beats per minute); however, one of ordinary skill in the art can select an alternative pulse rate based on the type and condition of organ that is being perfused.

In some examples, the disclosed methods utilize a dual perfusion technique, where the organ is perfused using simultaneous pulsatile and continuous flow. For example, the liver has two different blood supplies; the hepatic artery, which carries oxygenated blood from the circulatory system and the hepatic portal vein, which carries blood from the gut to the liver. Therefore, in some examples, the disclosed methods include pulsatile flow perfusion of a liver through the hepatic artery and continuous (or non-pulsatile) flow perfusion of the same liver through the portal vein that more closely mimics venous blood flow. In some examples, the perfusion pressure through the hepatic artery is about 10-25 mm Hg (such as about 12-25 or about 15-20 mm Hg) with a pulse of about 50-70 beats per minute (about 55-65 or about 60 beats per minute) and an amplitude of about 20%. The perfusion through the portal vein is about 2-5 mm Hg, such as about 2-4 or 3-4 mm Hg. In some examples, the hepatic artery flow is about 50-150 ml/min (such as about 50-125, 60-110, 75-100, 85-95, or about 90 ml/min) and the portal vein flow is about 200-300 ml/min (such as about 225-275, 230-270, 240-265, or about 260 ml/min) One of ordinary skill in the art can select appropriate pressures and flows for perfusion of the liver or other organs.

In some examples, the perfusate exits the organ from one or more veins (such as the vena cava). For example, the methods can include passive venous drainage into the perfusion reservoir. In other examples, a catheter is inserted in a vein, for example for selective collection of fluid samples. The method can also include sample collection through side ports in the perfusion device (for example, for random sample collection).

Devices or systems that can be used in the disclosed methods are also known to one of ordinary skill in the art. Such devices include one or more chambers for holding an organ and a perfusion solution (such as the solutions disclosed herein) and one or more pumps (for example, one or more rotary pumps or peristaltic pumps) for delivery of the perfusion solution to the organ. Such devices also include one or more means to regulate temperature of the perfusion solution, such as one or more heat exchangers and one or more means to oxygenate the perfusion solution (such as an oxygenator in the perfusion circuit). In one example, the device includes a disposable unit including one or more pump heads (such as one or more centrifugal pump heads with magnetic coupling), one or more oxygenators with an integrated heat exchanger, one or more pressure sensors, connecting tubing, and a reservoir which holds the organ and perfusion solution. The organ is connected with the connecting tubing by one or more cannulas. The one or more pumps can perfuse the organ via pulsatile or continuous (such as non-pulsatile) pressure. The device also includes one or more thermo-electric elements (for example, Peltier devices) in combination with a water pump. Water of the required temperature is pumped through the heat exchanger in the oxygenator in the disposable unit. In some examples, the machine perfusion device includes a perfusion liquid reservoir containing a perfusion solution disclosed herein (such as a perfusion solution described in Tables 1, 2, or 5).

In some examples, the device (such as the disposable unit) may include one or more ports for introducing additional substances into the perfusion solution and/or for sampling the perfusion solution during perfusion of an organ. The device may also include one or more displays which provide information regarding perfusion pressure, flow, temperature, and other information. Thus, in some examples, the disclosed methods include monitoring characteristics of the perfusion solution during machine perfusion of an organ (such as pH, $pO_2$, $pCO_2$, oxygen saturation, mitochondrial function, lactate production, enzyme function, bile production, urine production, and so on). The parameters measured may depend on the organ being perfused, for example, bile production and liver function indicators (such as ALT, AST, and bilirubin levels) can be monitored if the organ is a liver, while urine production can be measured if the organ is a kidney.

Exemplary devices are available from Organ Assist, Groningen, Netherlands (such as Kidney Assist or Liver Assist), Organ Recovery Systems, Itasca, Ill. (such as Life-Port kidney transporter or liver transporter), Transmedics, Andover, Mass. (such as the heart or lung Organ Care System), OrganOx, Oxford, UK (such as OrganOx Metra), and XVIVO Perfusion Engelwood, Colo. Exemplary devices and systems are also described in U.S. Pat. Nos. 6,994,954; 6,953,655; 6,977,1420; 7,678,563; 7,811,808; 7,897,357; 8,268,547; 8,268,612; and 8,287,580; U.S. Pat. Publ. No. 2010/0028850; and International Pat. Publ. No. WO 2009/041806; all of which are incorporated herein by reference in their entirety. One of ordinary skill in the art can identify additional organ perfusion devices or systems that can be used with the methods and solutions disclosed herein.

The following examples are provided to illustrate certain particular features and/or embodiments. These examples should not be construed to limit the disclosure to the particular features or embodiments described.

Example 1

Machine Perfusion with BMPS

This example describes liver transplantation performed with machine perfusion of the allograft with Belzer machine perfusion solution (BMPS) prior to transplant.

BMPS was initially developed for kidney preservation (e.g., Muhlbacher et al., *Transplant. Proc.* 31:2069, 1999; Kwiatkowski et al., *Transplant. Proc.* 33:913, 2001; Stubenitsky et al., *Transplant. Int.* 68:1469, 1999). BMPS was initially tested with the intention to determine its ability to sustain adequate flow though the tissues for a prolonged period of time (nine hours). A liver allograft was continuously perfused with BMPS for nine hours at 12° C. with a liver perfusion device (Organ Assist, Groningen, The Netherlands), which provides pulsatile perfusion of the hepatic artery and continuous flow to the portal vein, and subsequently transplanted into a porcine recipient. The recipient expired at the end of the operation, which was performed without a passive veno-venous bypass system. The cause of death was ventricular tachycardia, and it happened hours after graft implantation.

Figure 1B:
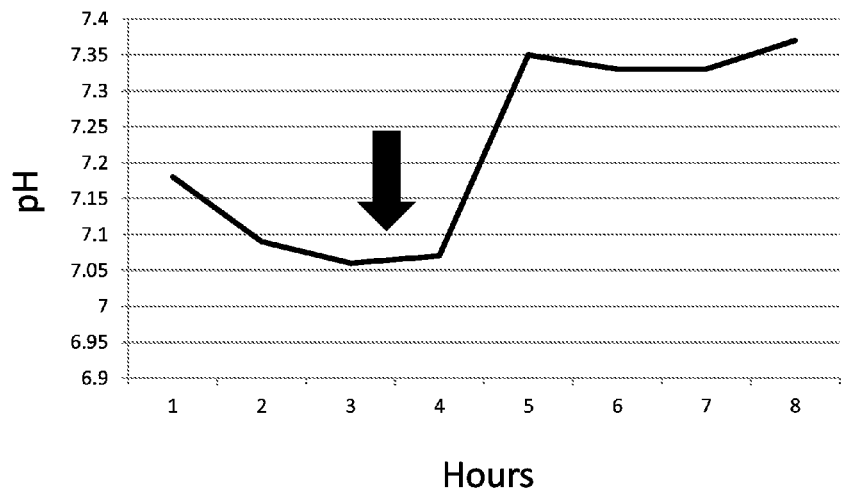
FIG. 1B is a graph showing pH of the perfusate over the course of a nine hour perfusion protocol. The arrow indicates infusion of 25 ml of 25 mEq $HCO_3$.

The liver perfusion device increased portal vein and hepatic artery flow, with stable pressure and temperature over nine hours (FIG. 1A). The flow increased over time due to progressive vasodilatation, which could be attributed to the temperature effect and the correction of initial metabolic acidosis with sodium bicarbonate. The pH of the perfusate dropped during the protocol (FIG. 1B). The initial metabolic acidosis was treated with an infusion of sodium bicarbonate (25 ml of 25 mEq $HCO_3$). Persistent metabolic acidosis requiring correction with sodium bicarbonate infusion was a constant finding when non-oxygen carrier solutions were utilized with the machine perfusion device.

Example 2

Development of a HBOC Solution

This example describes development of a HBOC solution with improved characteristics.

HEMOPURE as an acellular HBOC (OPK Biotech, Cambridge, Mass.) was chosen as a starting point due to its intrinsic ability to carry oxygen. HEMOPURE was tested as the perfusate for machine perfusion after initial dilution experiments were performed. HEMOPURE showed initially a rather low oncotic pressure and a high pH, in addition to the lack of chemical buffers and a powerful oncotic agent to sustain long term and effective tissue perfusion. BMPS (Table 3) was combined with HEMOPURE (Table 4) at 25%, 50%, and 75% dilutions (Table 5) as a way to achieve a target composition for the oxygen carrier solution for machine preservation. Since HEMOPURE had initially a high pH (7.92) and a low oncotic pressure (COP=26.8 mm Hg), the new solution contained a higher fraction of BMPS (75%) and a lower fraction of Hemopure (25%). The 3:1 BMO+PS:HEMOPURE dilution (referred to as BMPS/HBOC solution) was selected as having a composition with high oncotic pressure, normal osmolality, and effective oxygen carrier capabilities (Table 5) for machine perfusion of allografts prior to transplantation.

TABLE 3

| Belzer MPS | |
| --- | --- |
| pH (room temp.) | 7.517 |
| Osmolality (mOsm/kg) | 294 |
| COP (mm Hg) | 70.1 |
| $Na^+$ (mmol/L) | 93 |
| $K^+$ (mmol/L) | 21.1 |
| $Cl^-$ (mmol/L) | 10 |
| $Ca^{2+}$ (mmol/L) | <LOQ |

TABLE 4

| HEMOPURE | |
| --- | --- |
| pH (room temp.) | 7.92 |
| Osmolality (mOsm/kg) | 302 |
| COP (mm Hg) | 26.8 |
| $Na^+$ (mmol/L) | 150 |
| $K^+$ (mmol/L) | 4.2 |
| $Cl^-$ (mmol/L) | 115 |
| $Ca^{2+}$ (mmol/L) | 1.01 |

TABLE 5

| BMPS/HEMOPURE dilutions | |
| --- | --- |
| 25% BMPS/75% HEMOPURE (1:3 BMPS:HEMOPURE) | |
| pH (room temp.) | 7.82 |
| Osmolality (mOsm/kg) | 299 |
| COP (mm Hg) | 39.7 |
| $Na^+$ (mmol/L) | 134 |
| $K^+$ (mmol/L) | 8.9 |
| $Cl^-$ (mmol/L) | 87 |
| $Ca^{2+}$ (mmol/L) | 0.62 |
| 50% BMPS/50% HEMOPURE (1:1 BMPS:HEMOPURE) | |
| pH (room temp.) | 7.74 |
| Osmolality (mOsm/kg) | 299 |
| COP (mm Hg) | 50.7 |
| $Na^+$ (mmol/L) | 120 |
| $K^+$ (mmol/L) | 13.2 |
| $Cl^-$ (mmol/L) | 61 |
| $Ca^{2+}$ (mmol/L) | 0.39 |
| 75% BMPS/25% HEMOPURE (3:1 BMPS:HEMOPURE) | |
| pH (room temp.) | 7.62 |
| Osmolality (mOsm/kg) | 296 |
| COP (mm Hg) | 59.1 |
| $Na^+$ (mmol/L) | 105 |
| $K^+$ (mmol/L) | 17.3 |
| $Cl^-$ (mmol/L) | 36 |
| $Ca^{2+}$ (mmol/L) | 0.24 |

The new BMPS/HBOC solution showed adequate electrolyte composition (a sustained higher $Na^+/K^+$ ratio), higher levels of $Ca^{2+}$, and a sustained COP (59.1) while maintaining adequate osmolality (296 mOsm/Kg). The final pH (7.62) was more acceptable than the extremely high pH (7.82) showed initially by HEMOPURE.

The low fraction of HEMOPURE (25%) provided a good vehicle for oxygen transportation and $CO_2$ removal, in addition to sustaining low levels of methemoglobin. HEMPURE was also selected for its ability to have a long half-life (over 18 hours) in the circulation, stability at room temperature, and limited impact on complement, white blood cell, and platelet activation. The low fraction of HEMOPURE in this new solution is believed to minimize some of the adverse effects (e.g., vasoactivity, nephrotoxicity, interference with macrophage function, antigenicity to a xenogeneic hemoglobin, indirect complement activation through the kinin pathway, and neurotoxicity) initially seen after the clinical applications of this solution as a blood substitute. Without being bound by theory, it is believed that the BMPS/HBOC solutions disclosed herein favor oxygen diffusivity through the plasma by promoting an effective low viscosity solution containing a reduced concentration of HBOC.

Example 3

Organ Perfusion Device

The machine perfusion liver device (MPLD) was originally developed by Organ Assist (Groningen, Netherlands). An initial transplant experiment showed that the liver bowl (chamber for liver placement) was rather small for swine and human livers. Also, the cannulas utilized for arterial (hepatic artery) and venous (portal vein) access were not adequate for larger livers and could be a limiting factor for higher flows. A larger bowl and larger cannulas were subsequently developed. The new chamber was also equipped with an additional port to allow external bile drainage while under perfusion. This newly developed device was further utilized in all the experiments where the new solution (BMPS/HBOC) was tested.

Example 4

Liver Preservation Study Design

This protocol was intended to compare the current standard of care for liver preservation (cold static preservation with UW solution at 4° C. without oxygenation and flow) to machine preservation at sub-normothermic conditions (21° C.), performed with dual pressure (continuous at the portal vein and pulsatile at the hepatic artery) and under full oxygenation for an extended period of time. These experiments were designed to be performed within a nine hour period of cold ischemia time (CIT). This time frame has been shown as clinically relevant for liver transplantation in humans regarding short and long term graft function. Furthermore, a CIT of nine hours has been previously shown as a very challenging surgical model for porcine, since the mortality can be between 70 to a 100% in 7 days due to the induction of a moderate to severe ischemia/reperfusion (I/R) injury within the liver allograft.

The surgical protocol was approved by the IACUC, University of Pittsburgh. Landrace pigs (60-70 kg) received cadaveric liver transplants after the organs were recovered from heart beating donors under standard techniques for clinical organ recovery. This included full heparinization and active allograft flushing with over 5 L of cold (4° C.) UW solution through both the hepatic artery and the portal vein. The livers were subsequently transplanted into matched recipients after 9 hours of cold ischemia time (CIT).

The control group consisted of animals receiving their liver allografts after 9 hours of CIT under static hypothermic preservation with UW (which is the current standard of care for humans). The study group received their liver allografts after the same period of time (9 hours) but with the livers being preserved by sub-normothermic (21° C.) machine perfusion with the newly developed BMPS/HBOC solution (described in Example 2) under full oxygenation, dual flow (continuous through a cannula inserted in the hepatic artery and pulsatile through a cannula inserted in the portal vein) and full oxygenation. The perfusate exited the liver through the vena cava and flowed freely down to the bottom of the reservoir. The perfusion machine had side ports for random sample collection and a catheter was placed at the exit site into the vena cava for selected collection of fluid samples. The surgical model involved the use of passive veno-venous bypass as a way to sustain hemodynamic stability during the anhepatic phase. Heparin (2000 U) was given prior to cannulation and the bypass was kept in place for less than 1 hour.

The animals recovered in an ICU-like facility after the completion of the surgical procedure followed by extubation. All the animals received tacrolimus for immunosuppression. The end study necropsy was performed on post-operative day 5 (POD5) as per the protocol approved under previous FDA recommendations. All of the tissues were processed by transplant pathologists in a blind fashion.

The sample collection was performed as followed:
Clinical
   Intra operative course (reperfusion syndrome)
   Morbidity, mortality, ascites drainage, bile production
Labs
Liver biopsies
   Baseline, post procurement, 3, 6 and 9 hours during preservation, post reperfusion and 5 POD (end study necropsy)
Bile samples (post reperfusion and daily)
Perfusate (preservation solution)

Example 5

Control Group Liver Transplantation

This example describes liver transplantation in a control group of animals utilizing previously developed organ preservation solutions.

Two different solutions (HTK and UW) were initially tested in the control group. The animals underwent a full orthotopic liver transplantation procedure, where a brief period of passive veno-venous bypass (VVBP) was instituted during the anhepatic phase. The VVBP was utilized as a way to sustain normal hemodynamic conditions during the anhepatic phase, since the animals did not have end-stage-liver-disease and no collateral circulation which would allow adequate venous return while clamping both the portal vein (PV) and the inferior vena cava (IVC). A sustainable stage of hemodynamic stability during the anhepatic phase was an important feature for this model, since a transient period of hypotension would be an additional variable regarding allograft insult after organ reperfusion.

Seven animals were initially transplanted after a nine hour CIT period where the liver allografts were preserved with HTK solution (histidine-tryptophan-ketoglutarate solution; Essential Pharmaceuticals, Newtown, Pa.). All the animals experienced moderate to severe ischemia/reperfusion (I/R) syndrome and only 2/7 (28%) survived over a five day period after transplantation.

Six animals (control group—UW) were subsequently transplanted after a 9 hour period of cold static preservation, where UW solution at 4° C. was utilized as the preservation solution (current standard of care for clinical transplantation). The liver allografts were biopsied every 3 hours and perfusate samples for subsequent analysis were also obtained. The livers were flushed with 1 liter of cold (4° C.) lactate ringer (LR) after UW preservation and right before organ implantation. A liver biopsy was obtained after organ reperfusion. Bile samples were also collected.

Figure 2A:
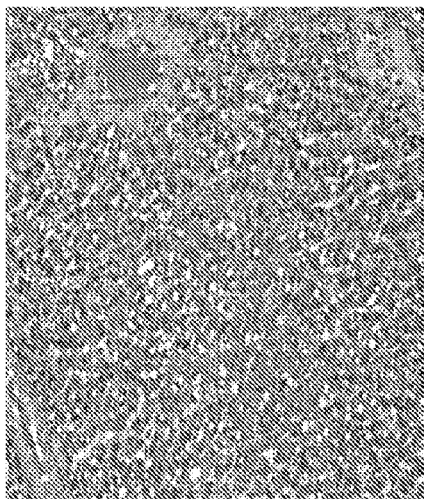
FIGS. 2A-D is a series of digital images of liver biopsies taken from two different control group animals (static preservation at 4° C. with UW solution).
Figure 2B:
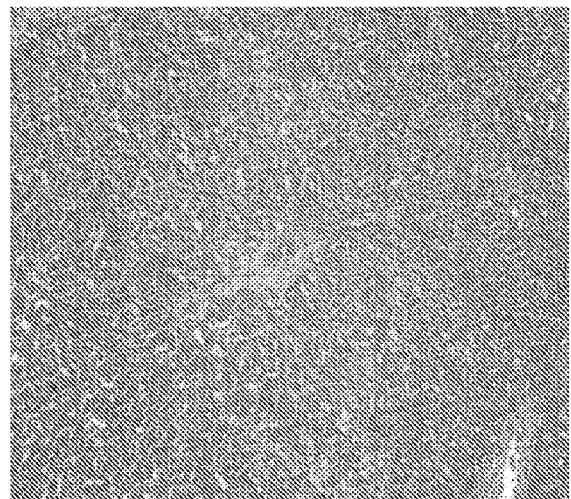
Figure 2C:
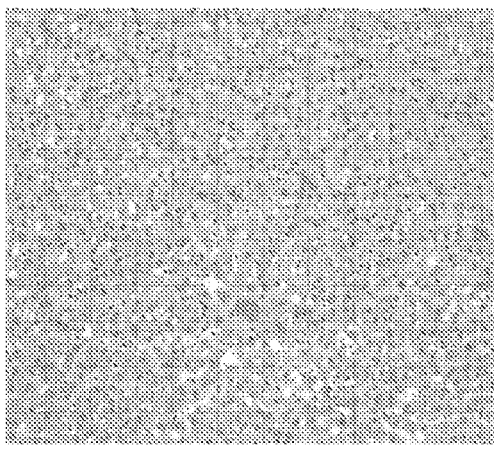
Figure 2D:
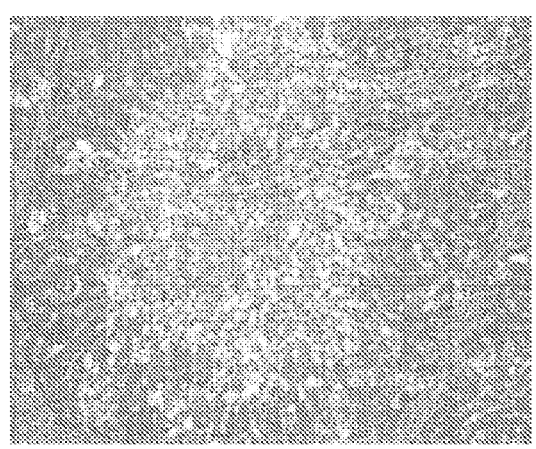

All the animals experienced different levels of I/R syndrome (from moderate to severe) and the mortality in 5 days was 83%. One animal died immediately after the surgical procedure from severe I/R injury. Most animals died within the first 3-4 days from acute liver failure leading into intractable lactic acidosis and respiratory failure (uncompensated respiratory alkalosis). Biopsies taken after organ reperfusion showed signs of diffuse microvesicular steatosis and centrilobular dropout compatible with moderate I/R injury (FIG. 2A) or mild microvesicular steatosis and centrilobular drop out compatible with mild I/R injury (FIG. 2C). The histological analysis of the liver allografts at the time of the end-study necropsy showed massive centrilobular necrosis and dropout compatible with moderate to severe I/R (FIGS. 2B and 2D). This illustrates the magnitude of I/R injury seen in the control group animals. Similar results were obtained with livers perfused with UW solution at 4° C., wherein only 20% 5 day survival was obtained (Fondevila et al., *Transplantation* 94:22-29, 2012).

Example 6

Study Group Liver Transplantation

This example describes liver transplantation in a group of animals utilizing a newly developed organ preservation solutions.

Six animals were transplanted after a 9 hour period of CIT, where the liver allografts were preserved with machine perfusion (MPLD) at 21° C. The preservation solution was the newly developed 3:1 BMPS/HBOC (described in Example 2) and all of the liver allografts were continuously oxygenated with a $FiO_2$=60% over a 7.5 hour period. The liver allografts were initially flushed with 1 liter of cold lactate ringer (LR) before placement within the device. The perfusion settings are shown in Table 6.

TABLE 6

Organ Assist liver device machine perfusion settings

| Variable | Settings |
|---|---|
| Portal vein flow | 232-272 ml/min (mean = 259) |
| Portal vein pressures | 3-4 mm Hg |
| Hepatic artery flow | 55-150 ml/min (mean = 91) |
| Hepatic artery pressures | 15-20 mm Hg (60 bpm, ampl. = 20%) |
| Temperature | 21° C. |
| Perfusion time (average) | 7 hours, 25 minutes |
| $FiO_2$ (range) | 40-80% (at 800 ml/min) |
| pH (range) | 7.26-7.5 |
| $NaHCO_3$ infusion | 10 cc at priming |
| $pO_2$ (range) | 335-707 mm Hg |

Perfusate samples were obtained every 30 minutes in the first 2 hours for standard arterial blood gases (ABG) tests with an IDDEXX machine in order to check for $pO_2$, $pCO_2$, pH, methemoglobin levels (%), electrolytes, and lactate. Perfusion data from one animal (study animal #6) is shown in Table 7. The liver allografts were biopsied every 3 hours and perfusate samples for subsequent analysis were also obtained. The livers were flushed with 1 liter of cold (4° C.) lactate ringer (LR) after machine preservation and right before organ implantation. A liver biopsy was obtained after organ reperfusion. Extensive histological analysis was performed after the end-study necropsy on the $5^{th}$ post-operative day.

Figure 3A:
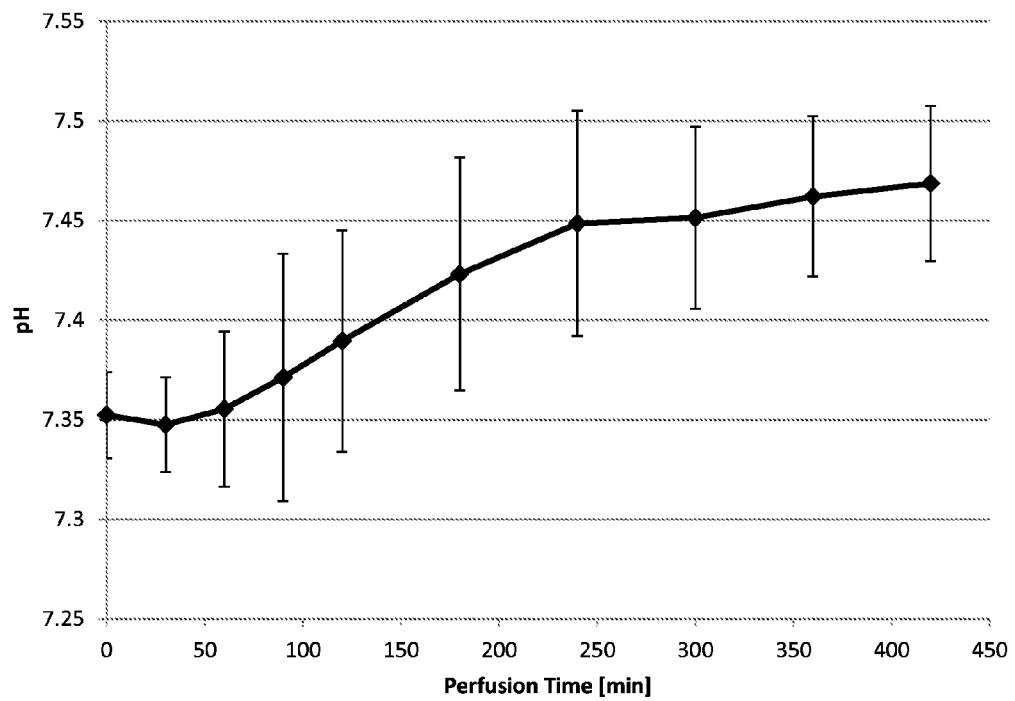
FIGS. 3A and B are a pair of graphs showing pH of the BMPS/HBOC perfusion solution during the course of machine perfusion at 21° C.
Figure 3B:
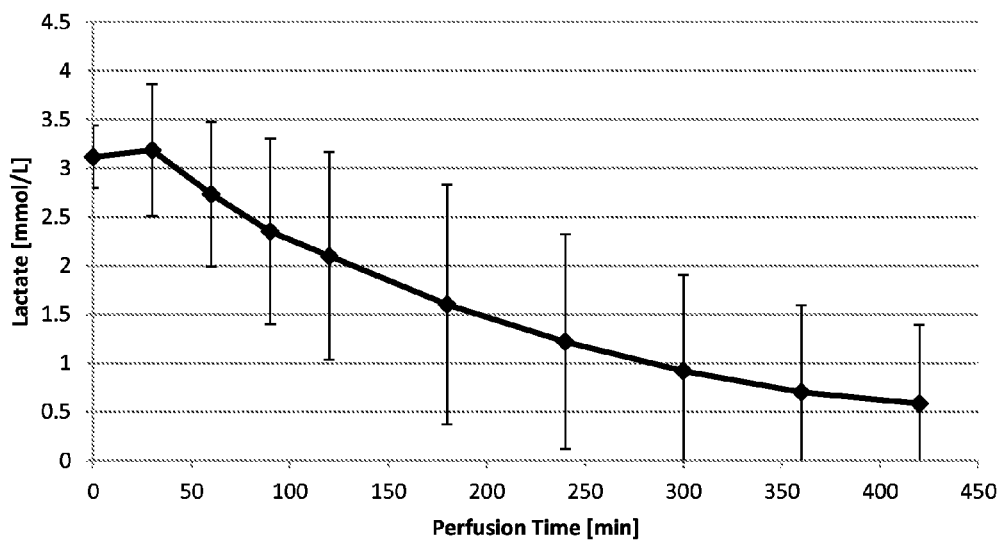

The pH of the perfusate remained stable while under perfusion with the BMPS/HBOC solution (FIG. 3A). There was no need to correct incipient metabolic acidosis that was seen with other solutions. In addition, the liver allografts made bile and cleared lactate (FIG. 3B) over a 7.5 hour period while under machine preservation with the BMPS/HBOC solution. This is a functional demonstration of the liver allograft aerobic activity while under machine preservation.

Figure 4A:
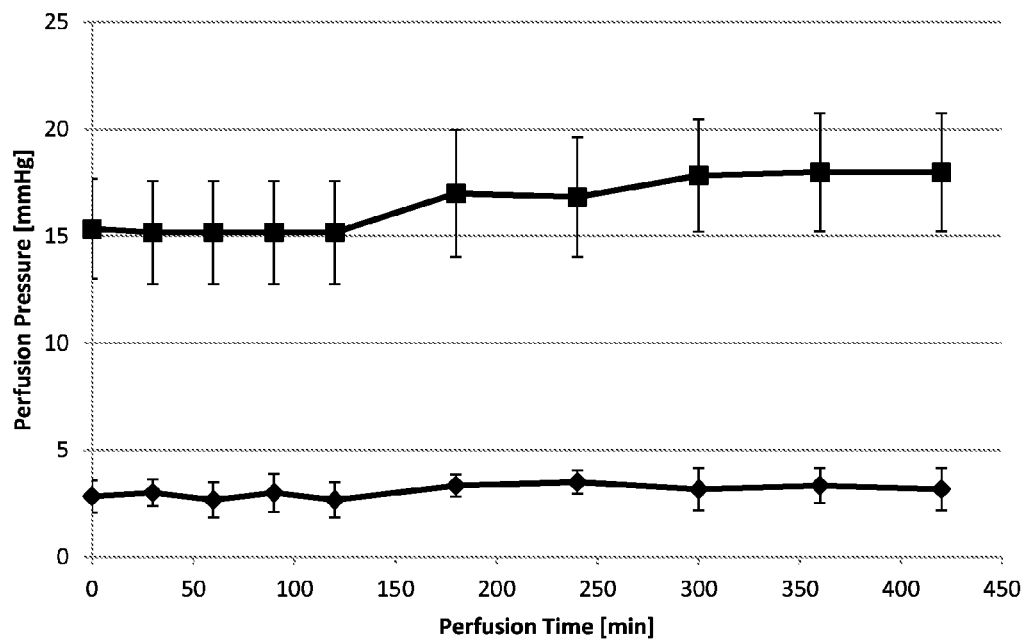
FIGS. 4A and B are a pair of graphs showing perfusion pressure (FIG. 4A) and flow (FIG. 4B) during machine perfusion. Squares, HA; diamonds, PV.
Figure 4B:
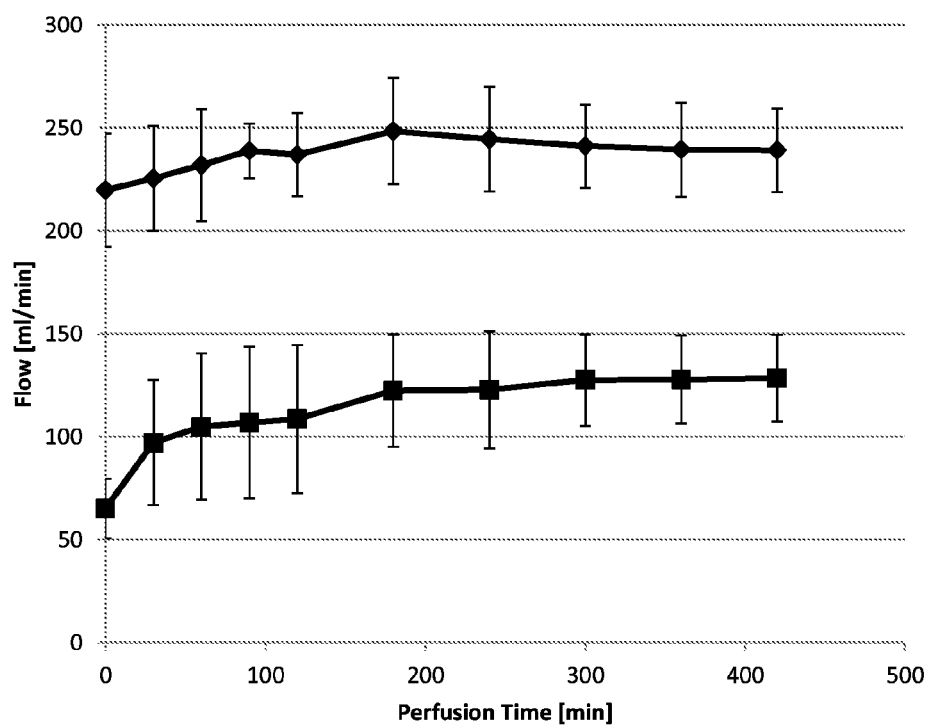
Figure 6:
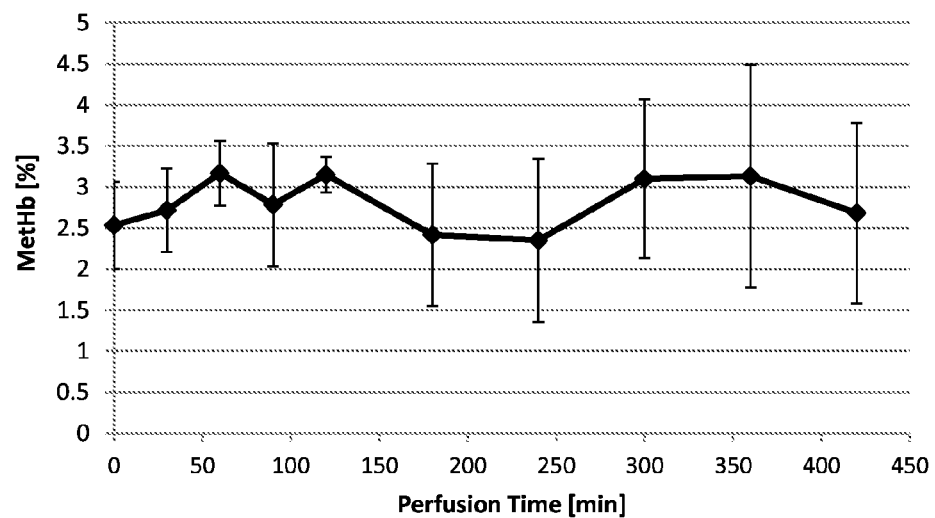
FIG. 6 is a graph showing methemoglobin (MetHb) levels in the perfusate during machine perfusion.

The temperature was maintained at 21° C. throughout the course of the perfusion. The average perfusion pressures for the HA (pulsatile flow) and the PV (continuous flow) are shown in FIG. 4A. There was an initial flow increase during perfusion caused by an intrinsic thermo effect leading into vasodilatation within the liver allograft (FIG. 4B). The flows were higher and more sustainable than those initially seen with non-oxygen carrier solution at 12° C. (Example 1). Subsequent biopsies (3, 6 and 9 hours) were able to show the integrity of the sinusoidal endothelial cell system, which has been previously reported as suboptimal under hypothermic conditions (Sanders et al., *Curr. Opin. Struct. Biol.* 6:534-540, 1996). Blood gas values were also measured during the course of the perfusion protocol. Arterial blood gas values were stable during the perfusion (FIG. 5A) and the livers were able to clear $CO_2$ while under machine perfusion at 21° C. (FIG. 5B). This indicated that the BMPS/HBOC solution was able to deliver an effective amount of oxygen to the liver allografts and to effectively remove $CO_2$ from the tissues while under perfusion, even though it contained only 3 g/dL hemoglobin. Finally, methemoglobin (MetHb) levels within the perfusate did not increase during machine perfusion (FIG. 6). These data show the stability of the HBOC in the machine perfusion solution. This parameter was measured because reports from previous clinical trials using HBOC have shown a potential increase in MetHb from extravasation of soluble hemoglobin into endothelial tissue, where it can rapidly react with NO and form MetHb (Jain et al., *Cryobiol.* 48:322-332, 2004).

The surgical procedure in the study group was about 1 hour (18%) shorter when compared to the control group. The study group animals had no clinical or laboratory signs of I/R syndrome and the operation could be completed safely shortly after graft reperfusion. The surgical data are shown in Table 8. The increased surgical time in the control group was due to increased time after liver reperfusion.

TABLE 7

Perfusion data from animal #6 while under machine perfusion with BMPS/HBOC solution

| Time (Min) | pH | $pCO_2$ | $pO_2$ | $FiO_2$ (%) | $HCO_3$ | K | Na | Ca | Lactate | Sat. (%) |
|---|---|---|---|---|---|---|---|---|---|---|
| Base | 7.35 | 4.4 | 514 | 60 | 3.3 | 17.5 | 110 | 0.25 | 2.8 | 93.4 |
| 0 | 7.384 | 0.8 | 546 | 60 | 3.3 | 18 | 110 | 0.25 | 3 | 94.6 |
| 30 | 7.383 | 3.7 | 548 | 60 | 3.1 | 18.3 | 109 | 0.25 | 2.9 | 93.9 |
| 60 | 7.408 | 5 | 565 | 60 | 3.0 | 18.5 | 108 | 0.25 | 2.1 | 93.9 |
| 90 | 7.452 | 3.9 | 516 | 60 | 3.0 | 18.6 | 108 | 0.25 | 1.2 | 93.7 |
| 120 | 7.474 | 6.7 | 509 | 60 | 3.0 | 18.7 | 108 | 0.25 | 0.7 | 94.1 |
| 180 | 7.494 | 5.7 | 551 | 60 | 3.0 | 14.4 | 108 | 0.25 | 0.1 | 94.3 |
| 240 | 7.509 | 5.3 | 517 | 60 | 3.0 | 18.2 | 109 | 0.25 | 0.1 | 94.4 |
| 300 | 7.503 | 6.7 | 536 | 60 | 3.0 | 18.1 | 108 | 0.25 | 0.0 | 93.8 |
| 360 | 7.484 | 7.3 | 528 | 60 | 3.0 | 18.0 | 108 | 0.25 | 0.0 | 94.3 |
| 420 | 7.482 | 6.4 | 530 | 60 | 3.0 | 17.9 | 109 | 0.25 | 0.0 | 94.1 |

TABLE 8

Comparison of control and study group surgical data

| | Control | Study |
|---|---|---|
| Operative time (min) | 331 | 270 |
| Warm ischemia time (min) | 28.2 | 32.6 |
| Bypass time (min) | 57 | 47 |
| Blood transfusions | 0/6 | 1/6 |
| Arterial complications | 0 | 0 |
| Venous complications | 0 | 0 |
| Intravenous fluids (L) | 13.5 | 7.9 |

Figure 7:
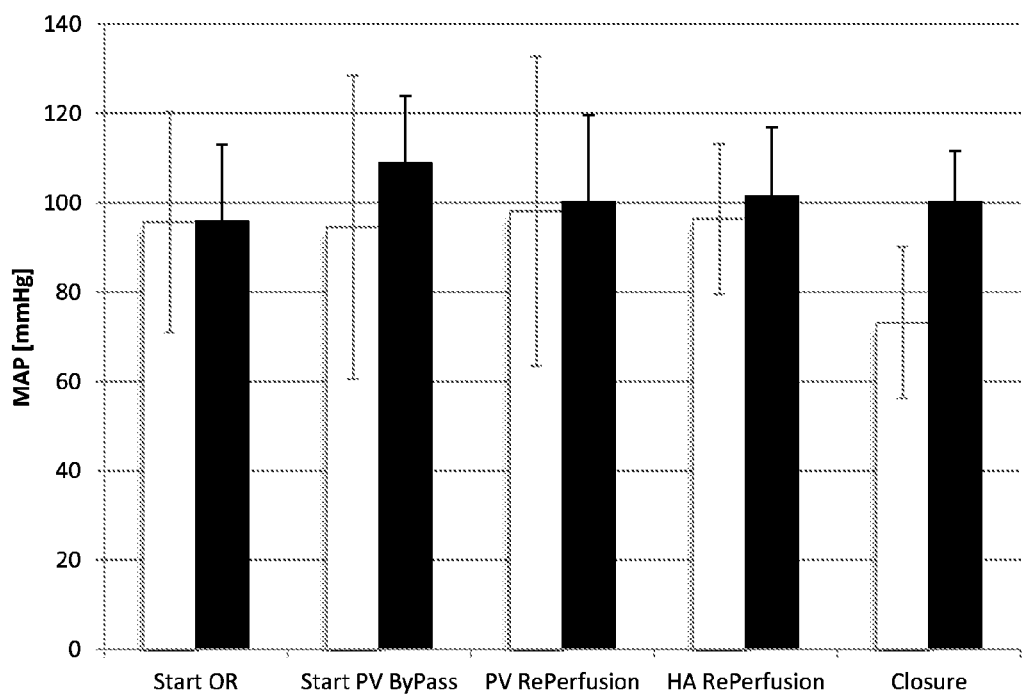
FIG. 7 is a graph showing intraoperative mean arterial pressure (MAP) during the liver transplant procedure. White bars, control group; black bars, study group.
Figure 8:
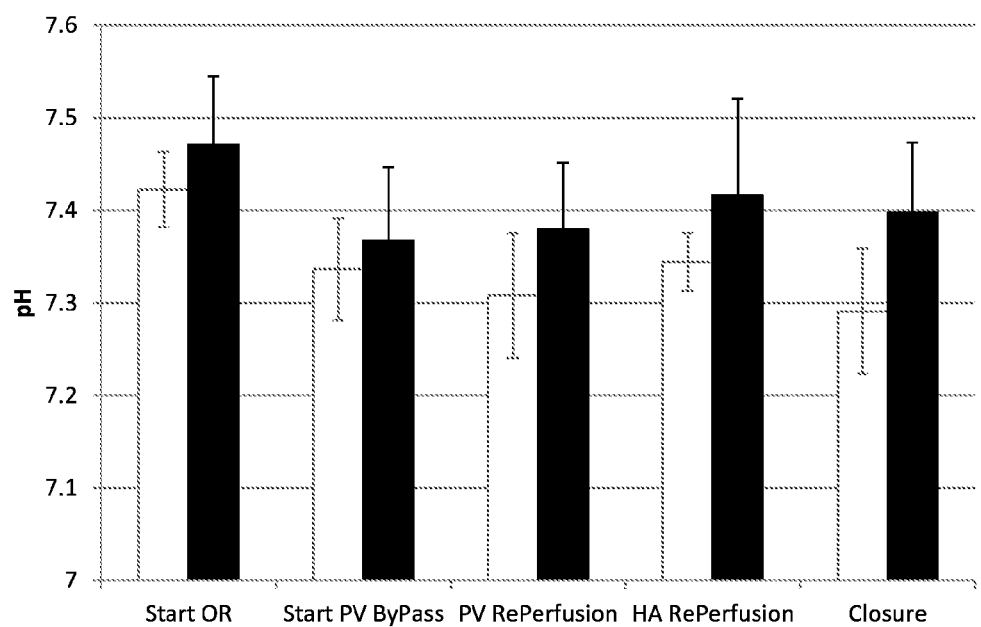
FIG. 8 is a graph showing intraoperative pH values obtained from ABGs taken during the liver transplant procedure. White bars, control group; black bars, study group.

The animals from the study group had none to mild signs of I/R syndrome immediately after graft implantation. The amount of intravenous fluids infused in the control group was 58% higher than the study group, since these animals presented with a higher degree of vasodilatation after liver allograft reperfusion. This illustrates the presence of persistent moderate to severe I/R injury in the control group, which subsequently was evident in a significantly higher mortality (83%) in 5 days when compared to the study group (0% mortality in 5 days). In addition, the control group animals showed a significant decrease in MAP after graft reperfusion compared with the study group (FIG. 7), in spite receiving 58% more intravenous fluid during the operation. This indicates the magnitude of the reperfusion syndrome experienced by the control group animals receiving liver transplants after 9 hours cold static preservation. There were no intraoperative blood transfusions in the control group. A single animal from the study group received a blood transfusion during the operation after having signs of hypotension immediately after the passive veno-venous bypass was started. There were no additional complications from the bypass procedure itself. Finally, the control group animals experienced a more pronounced metabolic acidosis after graft implantation (FIG. 8), in spite of receiving more volume and repeated infusions of sodium bicarbonate.

Figure 9A:
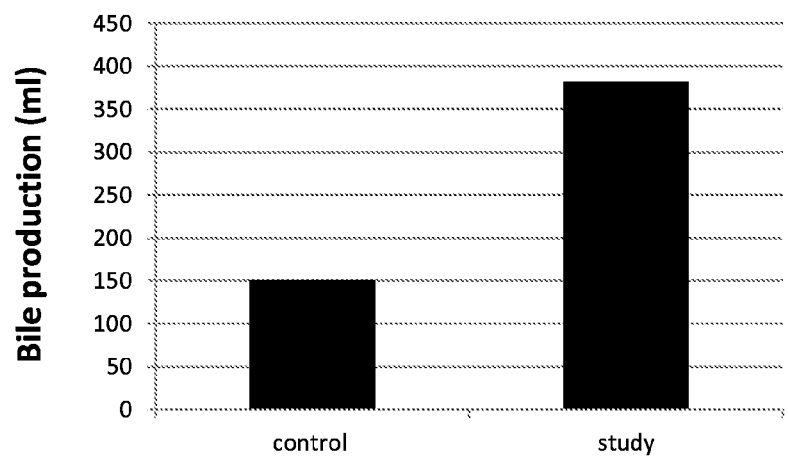
FIG. 9A-C is a series of graphs showing bile production (FIG. 9A), urine output (FIG. 9B), and ascites production (FIG. 9C) during the first 24 hours after liver transplantation for the control and study groups.
Figure 9B:
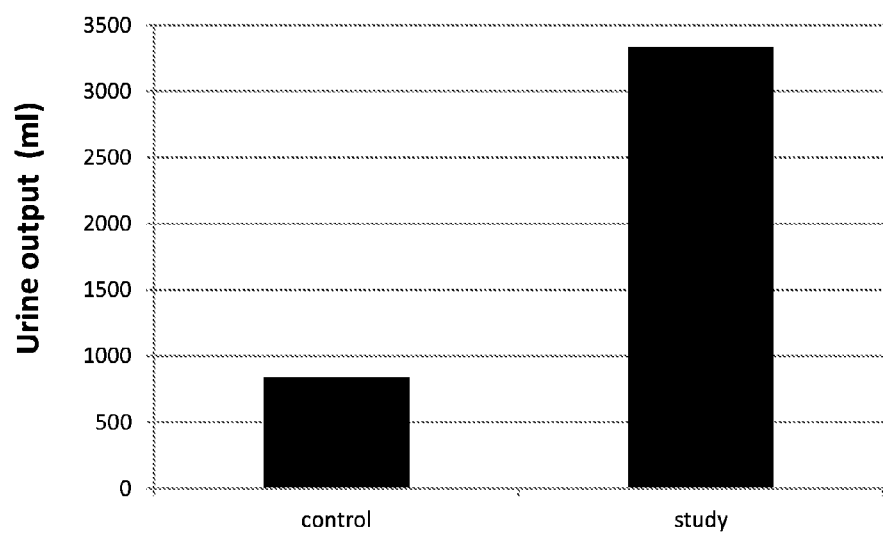
Figure 9C:
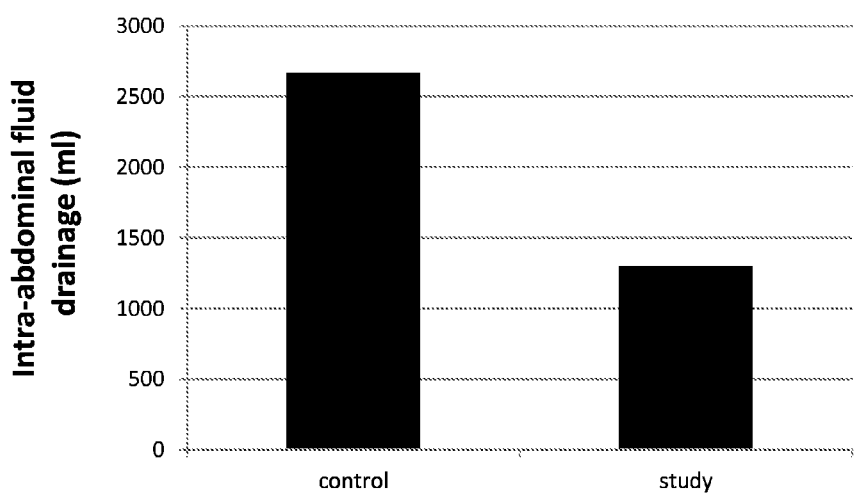

The animals from the study group made a significant amount of bile and urine when compared to the control group animals, in addition to a significantly lower amount of ascites during the post-operative period. A 2.5-fold increase in bile production was observed in the study group as compared to the control group (FIG. 9A). Bile production is a direct measure of liver function after graft implantation. The study group had a 3.9-fold increase in urine output when compared to the control group (FIG. 9B), where some animals developed progressive renal failure after the initial I/R syndrome (e.g., vasodilatation, hypotension, lactic acidosis, coagulopathy) after graft implantation. Finally, the control group had a 2-fold increase in the volume of ascites produced immediately after liver transplantation compared to the study group (FIG. 9C). The volume of ascites produced after liver transplantation is a direct sign of organ dysfunction. Taken together, the increased bile production and decreased ascites production in the study group demonstrated significantly better allograft function compared to the control group.

Figure 10:
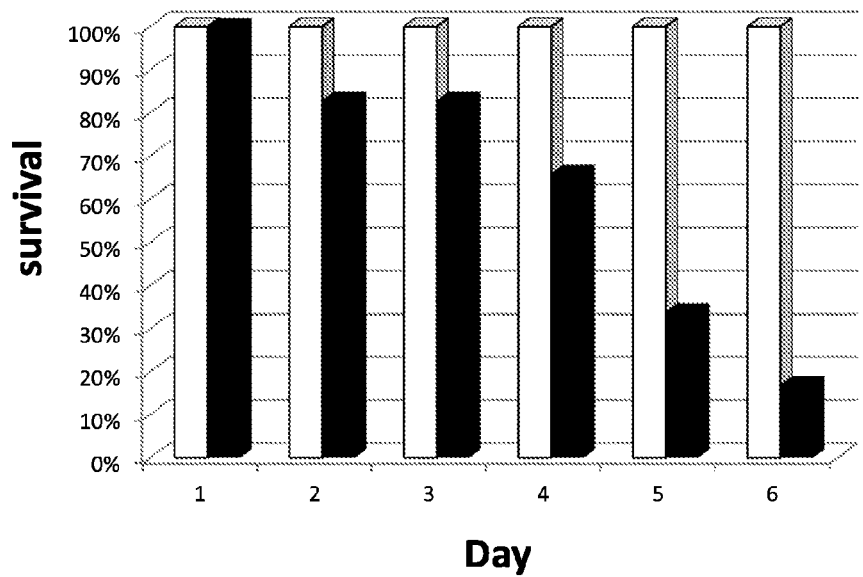
FIG. 10 is a bar graph showing percent survival for the study group (white bars) and control group (black bars) for the duration of the study (5 days).

The animals from the study group had 100% survival in 5 days (FIG. 10) and experienced no signs of liver allograft dysfunction and/or failure during the course of their initial follow up (5 days). The high mortality in the control group (83% in 5 days) was compatible with previously reported similar studies in the literature, where the mortality range for this model was found to be between 70 and 100% in 7 days.

Example 7

Liver Function Post-Transplantation

This example describes liver function and histology follow-up post-transplantation.

Figure 11:
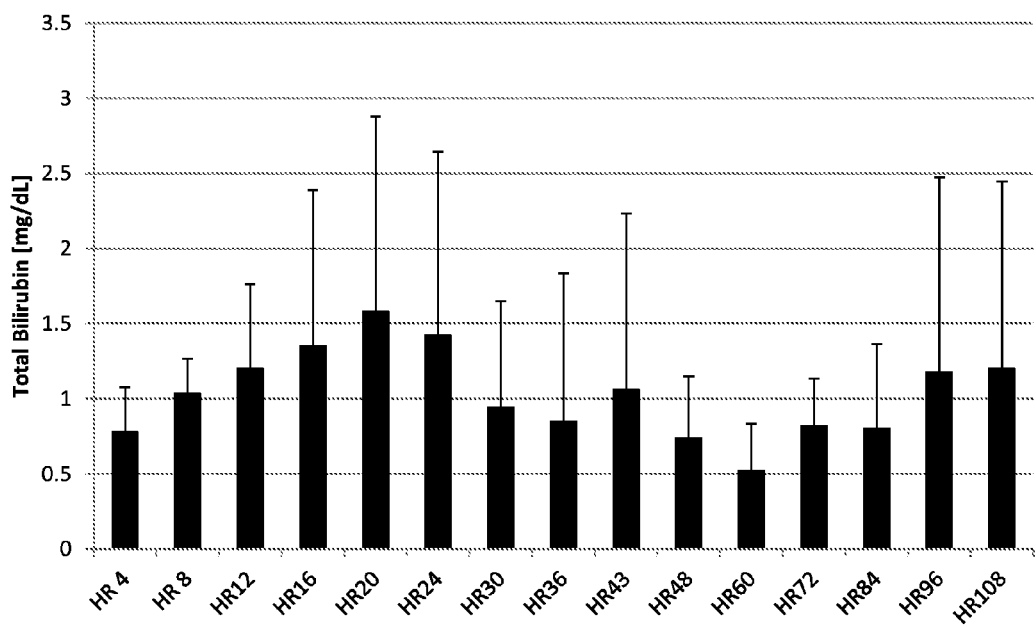
FIG. 11 is a graph showing total bilirubin (TBili) for the study group animals over the course of the five day follow-up.

A mild elevation of total bilirubin occurred post-operatively in the study group animals (FIG. 11). However, total bilirubin remained within normal range in the study group, in spite of the prolonged machine perfusion time.

Figure 12A:
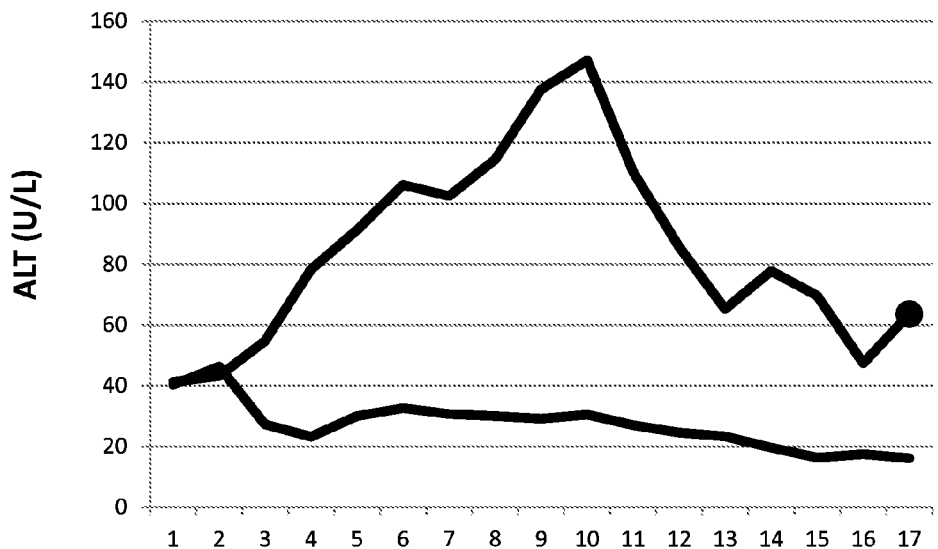
FIG. 12A to C are a series of graphs showing alanine transaminase (ALT) values (FIG. 12A), aspartate transaminase (AST) values (FIG. 12B), and lactate levels (FIG. 12C) for control (circles) and study (no symbol) groups during the 5 day follow-up period.
Figure 12B:
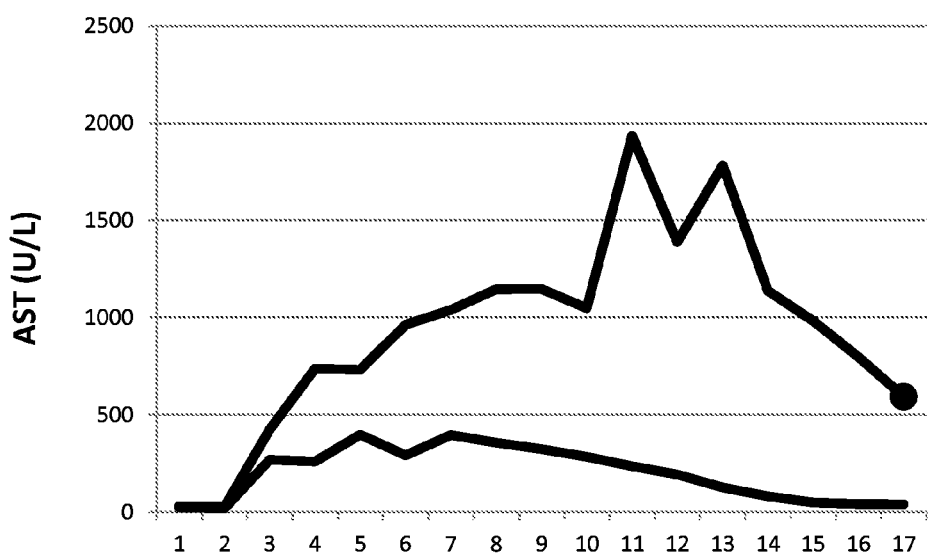
Figure 12C:
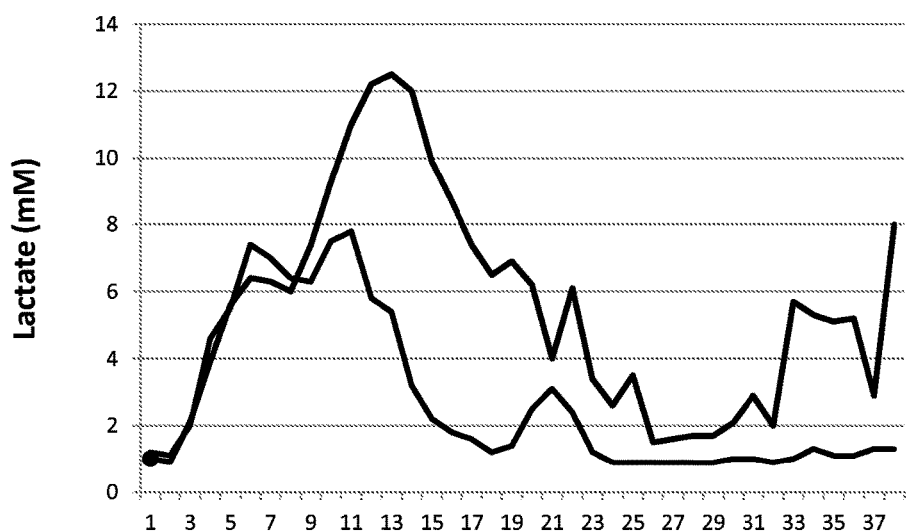

The analysis of the liver enzymes (alanine transaminase (ALT) and aspartate transaminase (AST)) showed a significant difference between the control and study groups. ALT and AST levels reflect the magnitude of hepatocellular insult/damage after liver transplantation. The liver allografts in the control group experienced a moderate to severe ischemic insult when compared to the animals in the study group. The control group animals had a moderate elevation of this enzyme while the study group animals ALT levels remained within the normal range (FIG. 12A), which is a remarkable finding for a full liver transplant model involving 9 hours of CIT. The AST levels were significantly higher in the control group and did not return to normal level for the entire duration of the experiment, while the study group animals had only a mild elevation of AST (FIG. 12B). The ALT and AST profiles show a significantly lower magnitude of hepatocellular damage experienced by the livers in the study group. The serum lactate levels were also significantly different between the two groups. Serum lactate measures the amount of lactic acid in the blood and is a sensitive and reliable indicator of tissue hypoperfusion and hypoxia. The serum lactate levels are directly related to the liver allograft function after liver transplantation. The study group had a mild serum lactate elevation followed by a prompt return to normal levels, while the control group had a major increase in the serum lactate levels, which remained high as the animals experienced liver allograft failure and death (FIG. 12C).

Figure 13A:
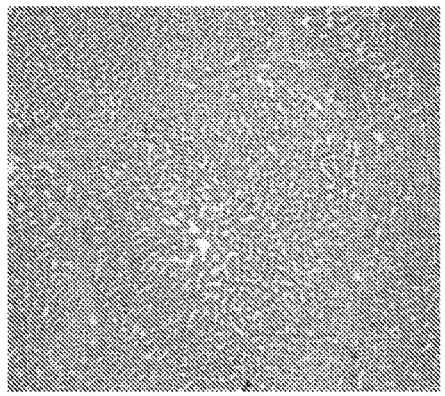
Figure 13B:
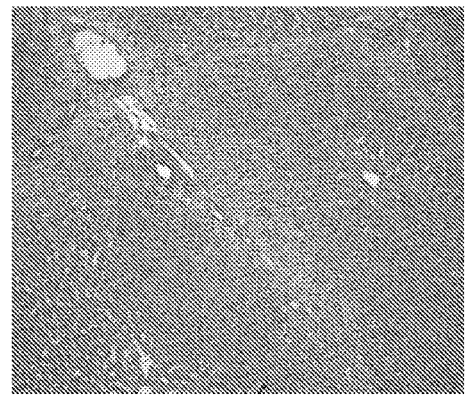

Contrary to the animals in the control group, all the biopsies taken from the study group animals were blindly reported as having a lower grade of I/R injury lesions (FIGS. 13A-E), which included all biopsies taken under machine perfusion, the post reperfusion biopsy and the final biopsy taken during the end-study necropsy (5th post-operative day). At the end of study necropsy, the liver allograft had no features of I/R injury and early signs of mild acute cellular rejection (FIG. 13E). In addition, all of the biopsies showed normal cytoarchitecture features of the liver allograft while under machine perfusion.

Figure 14:
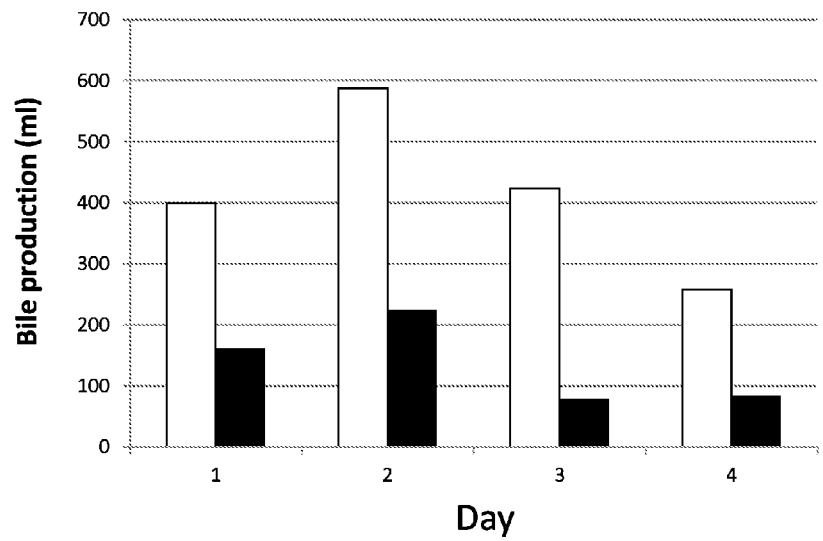
FIG. 14 is a bar graph showing post-operative daily bile production in study group (white bars) and control group (black bars).

The animals in the control group had a significantly lower amount of bile production than those in the study group (FIG. 14), a persistently higher amount of ascites and a significantly higher mortality. Bile production (volume and chemical structure) is one of the most important clinical parameters to determine liver function.

Example 8

Tissue Oxygenation and Mitochondrial Function

This example describes analysis of tissue oxygenation during perfusion and implantation and mitochondrial function during perfusion.

Tissue oxygenation was assessed by measuring the tissue oxygen tension (ptiO$_2$) with optical fluorescent technology (OxyLab™, Oxford Optronix, Oxford, UK). Two invasive O$_2$ sensors were inserted directly into the liver parenchyma through a tunnel developed by the initial insertion of 18Fr Angiocaths. The needle was withdrawn and the oxygen tissue probes were immediately inserted within the liver parenchyma. They were located within an inch from the liver capsule. The probes were secured with 6-0 PROLENE sutures and the readings were taken by a real time trace monitor displaying both the $pO_2$ and temperature.

The baseline reading for the liver $pO_2$ was initially taken at the beginning of the donor operation. This initial value was obtained with the animal under stable hemodynamic conditions while under general anesthesia (mechanical ventilation) and with a $FiO_2=100\%$. The results of the baseline readings (40-70 mmHg) were compatible with previous publications where the range on tissue $pO_2$ has been shown in normal animals. These data showed significant enhancement in tissue oxygenation while under machine preservation (Table 9). The OxyLab™ probes are calibrated for a range up to 200 mm Hg. The levels of tissue oxygenation in the liver allograft were consistently higher than 200 mm Hg while under machine perfusion.

TABLE 9

Tissue oxygen tension during transplantation procedure

|  | Tissue (mm Hg) | Perfusate ($FiO_2= 60\%$) (mm Hg) |
| --- | --- | --- |
| Baseline | 40-80 |  |
| Machine preservation | >200 | 400-500 |
| After organ transplantation | 40-80 |  |

Additional analysis was performed by a direct assessment of the mitochondrial respiratory control ratio (RCR). Fresh tissue was obtained from liver biopsies taken according to the initial protocol (baseline, post procurement, 3 hours, 6 hours, 9 hours and post reperfusion). Liver mitochondria were isolated by differential centrifugation and tested in a sealed chamber fit with a Clark-type oxygen electrode (Instech Corp., Plymouth Meeting, Pa.) connected to a data recording device (DATAQ Systems).

Figure 15A:
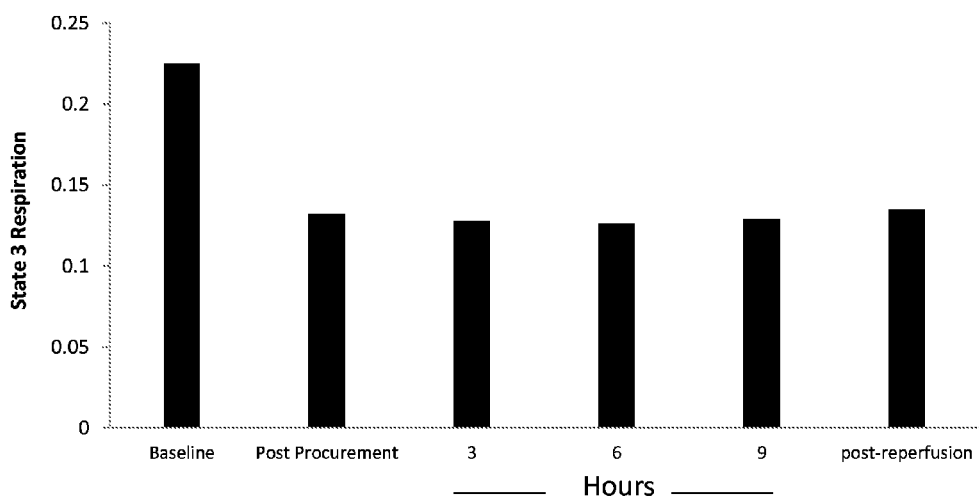
FIGS. 15A-C are a series of graphs showing mitochondrial function during machine perfusion in study group at baseline, post-procurement, 3, 6, and 9 hours of perfusion, and post-reperfusion.
Figure 15B:
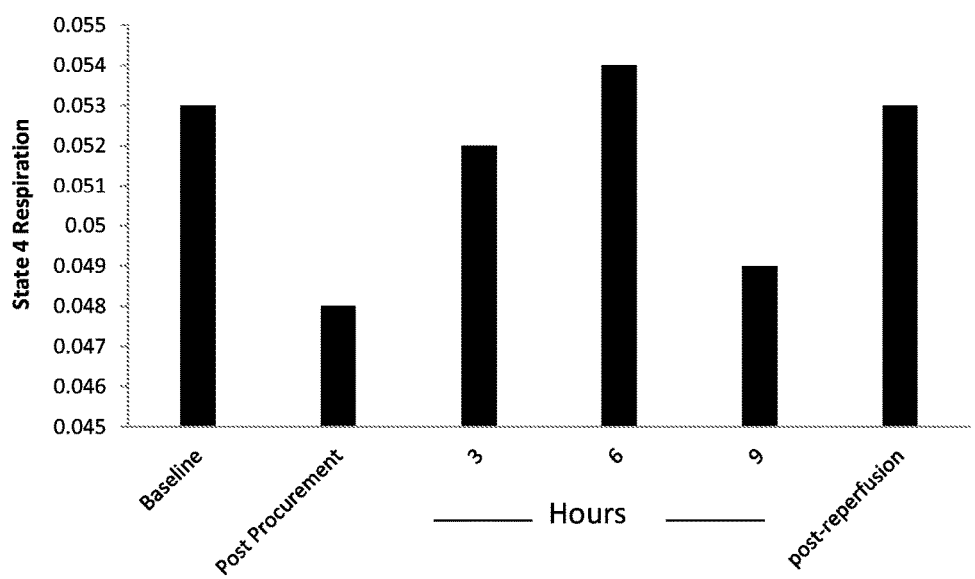
Figure 15C:
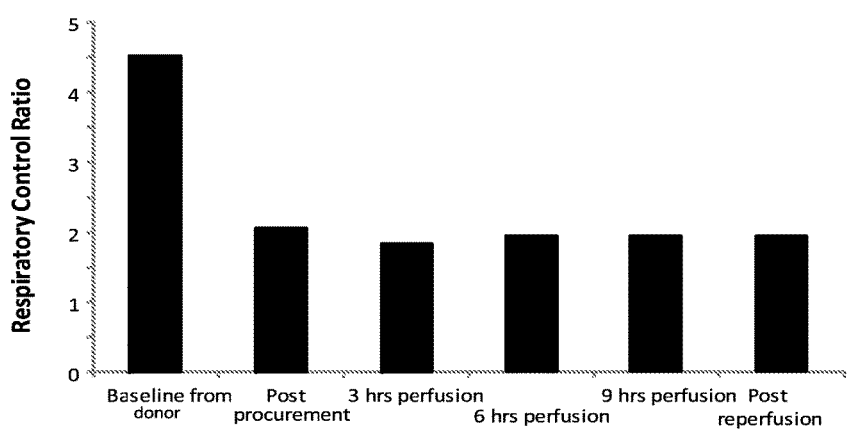
Figure 16A:
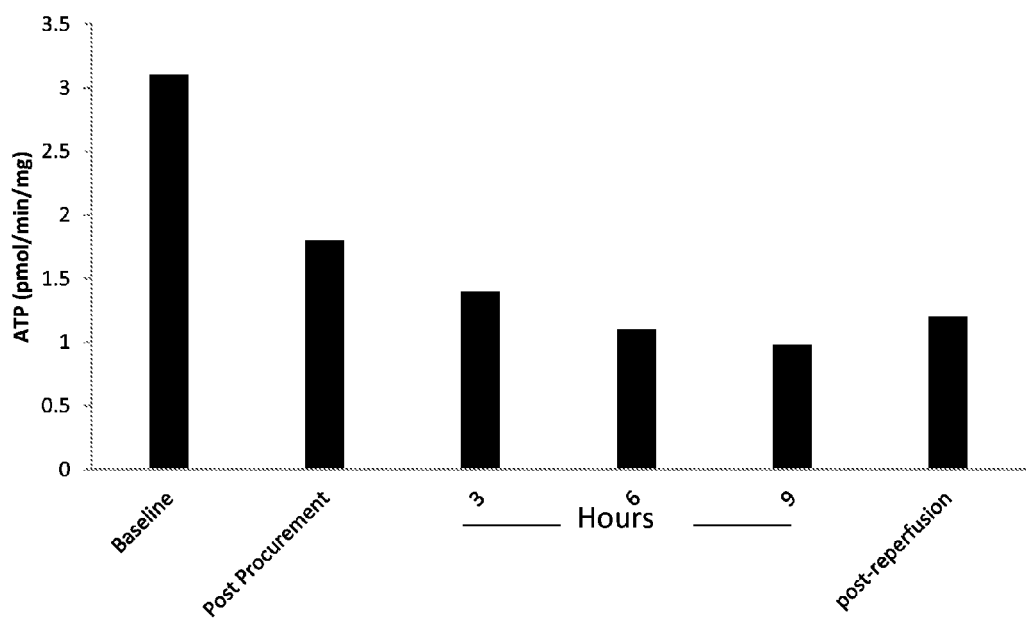
FIG. 16A is a graph showing ATP generation by allograft mitochondria during machine perfusion at baseline, post-procurement, 3, 6, and 9 hours of perfusion, and post-reperfusion.
Figure 16B:
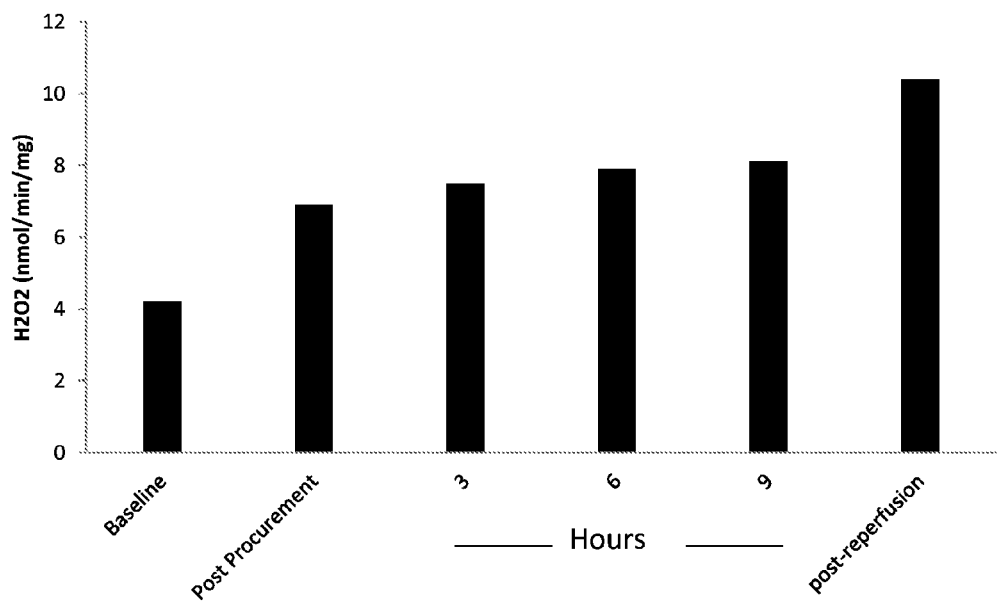
FIG. 16B is a graph showing production of reactive oxygen species during machine perfusion at baseline, post-procurement, 3, 6, and 9 hours of perfusion, and post-reperfusion.

State 3 respiration (FIG. 15A), state 4 respiration (FIG. 15B), and RCR (FIG. 15C) were measured in fresh liver tissue obtained at 3, 6, and 9 hours during machine perfusion and after liver allograft reperfusion. These findings revealed completely intact function of the mitochondria while the liver was maintained in an ex vivo environment and being perfused with the new BMPS/HBOC solution with a $FiO_2=60\%$. There was also sustained ATP generation by the liver allograft mitochondria while under perfusion with the BMPS/HBOC solution at 21° C. (FIG. 16A). Finally, in spite of being away from blood circulation for over 7.5 hours, the liver allograft tissue was adequately perfused and oxygenated, and there was only a mild increase in ROS production (two-fold) by the isolated mitochondria (FIG. 16B).

These additional dynamic tests demonstrated that the new system involving machine perfusion under full oxygenation paired with an oxygen-carrier solution was able to maintain mitochondrial function and promote effective tissue oxygenation ex vivo over a prolonged period of time (7.5 hours).

Example 9

Composite Tissue Allotransplantation

This example describes methods that can be used for composite tissue allotransplantation utilizing machine perfusion and the perfusion solution disclosed herein.

A swine vertical rectus myocutaneous (VRAM) flap model was chosen because it is a myo-adipo-cutaneous flap and comprises most CTA tissue components. The VRAM, a type II muscle flap, has two dominant vascular pedicles, either one of which can support the entire myocutaneous flap because of the presence of choke vessels. Also, the VRAM reflects a heterotopic CTA where the graft can be easily performed and accessible for clinical monitoring and sequential follow up interventions (hemodynamic, ischemia reperfusion and immune profile measurements), while avoiding the risk of mechanical pressure and automutilation.

Four groups (control and study) are used for ex vivo (Groups 1 and 2) and in vivo (Groups 3 and 4) perfusion/transplantation of VRAMs in SLA haplotyped MGH miniature swine donor/recipient pairs. Flap procurement and perfusion are performed according to the clinical standards under appropriate anesthetic and surgical sterile precautions. Flaps are perfused ex vivo via arterial perfusion with UW solution or BMPS/HBOC solution (described in Example 2) at 4° C. after cross clamp.

In control and study groups, UW or BMPS/HBOC is used for ex vivo flap perfusion over the same amount of CIT (24 hours). The target flows are 50% of the normal in vivo values in order to avoid endothelial cell damage to the microvasculature. In study groups, the solution is fully oxygenated ($FiO_2=60\%$) and with pulsatile flow at 60 beats per minute for arterial perfusion of the flap. The machine perfusion device has a chamber where the flap is placed for the perfusion protocol, allowing passive venous drainage into the reservoir. The system is kept at 21° C. The flaps are biopsied every 3 hours and the perfusate is continuously monitored (ABG protocol) throughout the entire MP protocol. Two groups receive in vivo transplantation of the flaps after the perfusion protocol with standard post-transplant immunosuppression (tacrolimus, 0.3 mg/kg/day; Cellcept® (mycophenolate mofetil), 500 mg twice daily; and prednisone, 10 mg daily). Solumedrol (1 gram) is given intraoperatively prior to graft implantation. The animals have a central line catheter (Broviac) placed into the right internal jugular vein in order to allow daily blood sampling throughout the entire duration of the experiment. The animals are extubated in the operative room and recovered under intensive care unit standards following the procedure.

The VRAM flap is created by designing a 15×5-cm rectangular skin island just lateral to the midline, parallel to the long axis, and on the ventral surface of the pig overlying the choke zone vessels. The rectus muscle is delivered from the constraints of the rectus fascia, the muscle is divided at its distal insertion, and the deep inferior epigastric artery and veins are ligated. The flap is elevated from a distal to proximal location, with ligation of all segmental vessels, leaving only the superior epigastric vascular pedicle as the sole blood supply to the composite flap. The superior epigastric vascular pedicle is identified at the superior dorsal surface of the elevated myocutaneous flap. The rib cartilage overlying the vascular pedicle is carefully resected to provide full access to the proximal pedicle (internal thoracic artery and veins) of the VRAM rotational flap from its emergence from the thoracic cavity to where it enters the muscular portion of the flap. The muscular side of the flap with the superior epigastric artery is apparent from its emergence from the thoracic cavity to its distal perpendicular segmental muscular branches.

Analyses include 4 mm punch biopsies of skin, skeletal muscle and adipose tissue will be performed at baseline (before ischemia), and then every 3 hours during the 24 hour perfusion for Groups 1 and 2. Similar punch biopsies of skin, muscle and subcutaneous fat are performed on alternate days in Groups 3 and 4. All component flap tissues (included nerve and vessel) are also be collected at euthanasia (14 day end point for Groups 3 and 4). Tissue samples are formalin fixed for paraffin embedding, flash frozen for immunohistochemistry and also stored in RNA Later. Every sample is evaluated for I/R injury-induced alterations: perivascular edema, erythrocyte extravasation, leukocyte adhesion and infiltration, intraluminal thrombi, and loss of endothelial layer in medium-sized vessels as indicators of endothelial dysfunction and vascular leakage. Also, hypereosinophilia and nuclear changes such as pyknosis, karyorrhexis, or karyolysis as signs of necrosis and apoptosis are quantified. In muscle, disrupted muscle fibers, disturbed or lost cross striations, and decomposed endomysium and epimysium are distinguished from hypothermia- and fixative-induced fiber shortening and thus gap formation as indicator of muscle edema. In flap nerves, intramyelinic and endoneural edema, compression-induced myelin damage, and axonal vacuolization separated distinguish I/R-induced injury from myelinolysis and Wallerian degeneration due to axotomy. In vessels, fragmentation of lamina elastica interna or externa and involvement of vasa vasorum are assessed. Every criterion is scored from 0-3 (0=absence, 1=scarce, 2=intermediate, and 3=maximal presence) and summed up to a histologic injury severity score (HISS, min.=0, max.=24). All the tissues are blindly analyzed by a group of experienced pathologists.

Blood samples are obtained daily until end point in Groups 3 and 4. Serum and tissue levels of cytokines such as IL-1β, IL-6, IL-8, TNF-α, and IL-10 levels are measured by multiplex suspension array. Similarly, serum and tissue levels of MCP-1, growth factors, complement activation products and plasma levels of MCP-1, VEGF, PDGF-bb, bFGF, C3c, C5a, and sC5b-9 are also analyzed at different time points. Serum complement activation is assessed using the hemolytic assay (CHSO) using antibody-sensitized sheep red blood cells (108 cells/mL); incubated with porcine serum diluted 1:200 in Veronal buffered saline containing $Mg^{2+}$ and $Ca^{2+}$ and further incubated for 60 min at 37° C. in a shaking water bath.

Cryoconserved biopsies are cut into 5-µm-thick sections and air-dried for 30-60 min. They are stained for markers of endothelial cell activation due to UR injury such as HSPG, preservation of the anticoagulant and anti-inflammatory EC surface throughout the experimental protocol (vWF), and activation of the complement pathway due to I/R injury, namely C3c, C5a, and sC5b-9.

Cytokines and complement split products are measured using multiplex xMAP® technology (Luminex Corp, Austin, Tex.) sandwich immunoassay. Serum IL-1β, IL-6, IL-8, IL-10, and TNF-α will be measured. Microbeads (Luminex Corp) carrying different fluorochrome codes are coupled with monoclonal antibodies specific for the respective analyte. Capture antibodies for the above-mentioned antigens (all from R&D Systems, Minneapolis, Minn.) are coupled to the beads using Bio-Plex amine coupling kit (Bio-Rad Laboratories, Hercules, Calif.). The following parameters are measured by Bio-Plex in EDTA plasma using antibodies from anti-human ELISA kits cross-reacting with the respective porcine antigens: bFGF, PDGF-bb, and VEGF. Furthermore, the following specific capture/detection antibody pairs are used: C3c and C3c-FITC, sC5b-9 (anti-C9/anti-C6), C5a, and MCP-1. For C5a and sC5b-9 the fluorescence intensity is used for statistical analysis.

In some examples, the CTA transplantation is considered successful if an enhancement in tissue preservation regarding neurologic and muscular integrity and function is achieved compared with the control group.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method for machine perfusion of a liver, comprising perfusing the liver through the hepatic artery in a pulsatile flow and through the portal vein in a continuous flow with a solution comprising 3-4 g/dL acellular cross-linked hemoglobin and 10-40 g/L hydroxyethyl starch in a physiologically acceptable medium, wherein the solution has a pH of about 7.55-7.85 at room temperature, an osmolality of about 290-300 mOsm/kg, and a colloid osmotic pressure of about 35-65 mm Hg, wherein the solution is oxygenated, and wherein the solution and the organ are maintained at a temperature of about 21° C. throughout the perfusion.

2. The method of claim 1, wherein the solution comprises about 3.25 g/dL cross-linked hemoglobin, 28.25 mM NaCl, 1 mM KCl, 18.75 mM $KH_2PO_4$, 60 mM sodium gluconate, 6.75 mM sodium lactate, 3.75 mM magnesium gluconate, 0.725 mM $CaCl_2$ dihydrate, 15.62 mM NaOH, 3.75 mM adenine, 7.5 mM dextrose, 2.25 mM glutathione, 7.5 mM HEPES, 3.75 mM ribose, 22.5 mM mannitol, 37.5 g/L hydroxyethyl starch, and 50 mg/dL N-acetyl-L-cysteine.

3. A method for machine perfusion of an organ, comprising perfusing the organ with a solution comprising 3-4 g/dL acellular cross-linked hemoglobin and 10-40 g/L hydroxyethyl starch in a physiologically acceptable medium, wherein the solution has a pH of about 7.55-7.85 at room temperature, an osmolality of about 290-300 mOsm/kg, and a colloid osmotic pressure of about 35-65 mm Hg, wherein the solution is oxygenated, and wherein the solution and the organ are maintained at a temperature of about 21° C. throughout the perfusion.

4. The method of claim 3, wherein the organ comprises one or more of a heart, lung, liver, kidney, pancreas, small intestine, limb, extremity, tissue graft, or portion thereof.

5. The method of claim 3, wherein at least a portion of the solution is delivered to the organ in a pulsatile flow.

6. The method of claim 3, wherein the solution is oxygenated with a gas mixture having an $FiO_2$ of 40-80%.

7. The method of claim 3, wherein the organ is a liver and the solution is delivered to the liver through the hepatic artery in a pulsatile flow and to the portal vein in a continuous flow.

8. The method of claim 7, wherein the hepatic artery pressure is about 15-20 mm Hg.

9. The method of claim 7, wherein the portal vein pressure is about 3-5 mm Hg.

10. The method of claim 3, wherein the method comprises perfusing the organ prior to transplantation, perfusing the organ during surgery or treatment, or perfusing the organ prior to or during collection of cells from the organ.

11. The method of claim 1, wherein the solution comprises 3-4 g/dL cross-linked hemoglobin, 25-85 mM NaCl, 1-3 mM KCl, 6-20 mM $KH_2PO_4$, 20-70 mM sodium gluconate, 5-21 mM sodium lactate, 1-4 mM magnesium gluconate, 0.6-1.2 mM $CaCl_2$ dihydrate, 11-16 mM NaOH, 1-4 mM adenine, 2-8 mM dextrose, 0.5-3 mM glutathione, 2-8 mM HEPES, 1-4 mM ribose, 7-30 mM mannitol, 10-40 g/L hydroxyethyl starch, and 40-160 mg/dL N-acetyl-L-cysteine.

12. The method of claim 3, wherein the solution comprises 3-4 g/dL cross-linked hemoglobin, 25-85 mM NaCl, 1-3 mM KCl, 6-20 mM $KH_2PO_4$, 20-70 mM sodium gluconate, 5-21 mM sodium lactate, 1-4 mM magnesium gluconate, 0.6-1.2 mM $CaCl_2$ dihydrate, 11-16 mM NaOH, 1-4 mM adenine, 2-8 mM dextrose, 0.5-3 mM glutathione, 2-8 mM HEPES, 1-4 mM ribose, 7-30 mM mannitol, 10-40 g/L hydroxyethyl starch, and 40-160 mg/dL N-acetyl-L-cysteine.

\* \* \* \* \*